United States Patent
Jin

(10) Patent No.: US 11,975,048 B2
(45) Date of Patent: *May 7, 2024

(54) LONG-ACTING FATTY ACID-CONJUGATED GnRH DERIVATIVES AND PHARMACEUTICAL COMPOSITIONS CONTAINING SAME

(71) Applicant: NOVEL PHARMA INC., Seoul (KR)

(72) Inventor: Dong Kyu Jin, Seoul (KR)

(73) Assignee: NOVEL PHARMA INC., Seoul (KR)

( * ) Notice: Subject to any disclaimer, the term of this patent is extended or adjusted under 35 U.S.C. 154(b) by 100 days.

This patent is subject to a terminal disclaimer.

(21) Appl. No.: 17/518,206

(22) Filed: Nov. 3, 2021

(65) Prior Publication Data
US 2022/0054593 A1 Feb. 24, 2022

Related U.S. Application Data

(60) Division of application No. 17/075,295, filed on Oct. 20, 2020, now abandoned, which is a continuation of application No. PCT/KR2019/003527, filed on Mar. 26, 2019.

(51) Int. Cl.
| | | |
|---|---|---|
| A61K 38/00 | (2006.01) | |
| A61K 38/24 | (2006.01) | |
| A61K 47/40 | (2006.01) | |
| A61P 15/08 | (2006.01) | |

(52) U.S. Cl.
CPC .............. *A61K 38/24* (2013.01); *A61K 47/40* (2013.01); *A61P 15/08* (2018.01)

(58) Field of Classification Search
CPC .......... A61K 38/24; A61K 47/40; A61P 15/08
See application file for complete search history.

(56) References Cited

U.S. PATENT DOCUMENTS

| | | | |
|---|---|---|---|
| 6,297,379 B1 | 10/2001 | Furuya et al. | |
| 6,664,369 B1 | 12/2003 | Lovas et al. | |
| 8,314,077 B2 | 11/2012 | Webb et al. | |
| 8,552,054 B2 | 10/2013 | Swindell et al. | |
| 8,951,973 B2 | 2/2015 | Burton et al. | |
| 10,646,484 B2 | 5/2020 | Laffont et al. | |
| 10,994,018 B2 | 5/2021 | Jin | |
| 2004/0022739 A1 | 2/2004 | Daniels et al. | |
| 2004/0022861 A1 | 2/2004 | Williams, III et al. | |
| 2004/0023867 A1 | 2/2004 | Daniels et al. | |
| 2006/0013776 A1 | 1/2006 | Daniels et al. | |
| 2006/0074027 A1 | 4/2006 | Saito et al. | |
| 2006/0189539 A1 | 8/2006 | Lovas et al. | |
| 2008/0027003 A1 | 1/2008 | Burov et al. | |
| 2009/0004273 A1 | 1/2009 | Gibson et al. | |
| 2012/0027805 A1 | 2/2012 | Burton et al. | |
| 2014/0155329 A1 | 6/2014 | Hsu et al. | |
| 2015/0148295 A1 | 5/2015 | Burton et al. | |
| 2015/0265535 A1 | 9/2015 | Yu et al. | |
| 2015/0297726 A1 | 10/2015 | Yoon et al. | |
| 2016/0000758 A1 | 1/2016 | Valia et al. | |
| 2018/0000943 A1 | 1/2018 | Tiberg et al. | |

FOREIGN PATENT DOCUMENTS

| | | | |
|---|---|---|---|
| CN | 102958512 A | 3/2013 | |
| CN | 107257681 A | 10/2017 | |
| JP | 6-122611 A | 5/1994 | |
| JP | 2001-139422 A | 5/2001 | |
| JP | 2002-531411 A | 9/2002 | |
| JP | 2004-2321 A | 1/2004 | |
| JP | 2011-201807 A | 10/2011 | |
| JP | 2012-509251 A | 4/2012 | |
| JP | 2016-504363 A | 2/2016 | |
| JP | 2016-508140 A | 3/2016 | |
| KR | 10-2001-0089538 A | 10/2001 | |
| KR | 10-2014-0086722 A | 7/2014 | |
| KR | 10-2014-0086741 A | 7/2014 | |
| RU | 2233284 C2 | 7/2004 | |
| RU | 2 543 327 C2 | 2/2015 | |
| WO | 00/32218 A1 | 6/2000 | |
| WO | 01/70227 A1 | 9/2001 | |
| WO | WO-2004012712 A1 * | 2/2004 | ............. A61K 31/56 |
| WO | 2004/030687 A1 | 4/2004 | |
| WO | 2005/074896 A1 | 8/2005 | |

(Continued)

OTHER PUBLICATIONS

Brunaldi et al. (Fatty acids are rapidly delivered to and extracted from membranes by methyl-cyclodextrin. Journal of Lipid Research vol. 51, 2010., p. 120-131).*

Office Communication ("Notice of Reasons for Refusal") dated Dec. 7, 2021 for counterpart Japanese Patent Application No. 2021-503113.

Golfo G. Kordopati et al., "A novel synthetic luteinizing hormone-releasing hormone (LHRH) analogue coupled with modified B-cyclodextrin: Insight into its intramolecular interactions"; Biochimica et Biophysica Acta, 1850 (2015), pp. 159-168 (11 pages).

Communication dated Nov. 10, 2021 from the Russian Federal Institute of Industrial Property in RU Application No. 2020142694/10.

(Continued)

*Primary Examiner* — Jeanette M Lieb
(74) *Attorney, Agent, or Firm* — Sughrue Mion, PLLC

(57) ABSTRACT

An aspect of the present disclosure pertains to a novel long-acting fatty acid-conjugated gonadotrophin-releasing hormone (GnRH) derivative and a pharmaceutical composition containing the same. A GnRH derivative of the present invention is expected to greatly contribute, through excellent bioavailability, increased half-life in blood, and remarkably high therapeutic effects on sex hormone-dependent disease, to the reduction in drug dosing frequency and dosage and the like in the treatment of sex hormone-dependent diseases. Particularly, the GnRH derivative can overcome the disadvantages of existing GnRH sustained-release preparations, which have the side effects of residual feeling and pain at the injection site.

16 Claims, 12 Drawing Sheets

Specification includes a Sequence Listing.

(56) References Cited

FOREIGN PATENT DOCUMENTS

| WO | 2008/075762 A1 | 6/2008 |
| WO | 2013/129879 A1 | 9/2013 |

OTHER PUBLICATIONS

Extended European Search Report dated Nov. 25, 2021 from the European Patent Office in EP application No. 19922178.9.

Dror Yahalom et al., "Synthesis and Bioactivity of Fatty Acid-Conjugated Gnrh Derivatives", Life Sciences, 1999, pp. 1543-1552, vol. 64, No. 17.

Ahmed Ezzat Ahmed et al., "Effects of methyl-beta-cyclodextrin on the release of luteinizing hormone, follicle stimulating hormone, prolactin and growth hormone from cultured bovin anterior pituitary cells", Journal of Experimental and Applied Animal Sciences, 2017, pp. 102-108, vol. 2, No. 2.

International Search Report for PCT/KR2019/003527 dated Dec. 26, 2019 [PCT/ISA/210].

Office Communication ("Notice of Reasons for Refusal") dated Jul. 6, 2021 for related Japanese Patent Application No. 2021-503113.

"Fatty acid conjugation", Pepscan, available online at https://www.pepscan.com/custom-peptide-synthesis/peptide-modifications/fatty-acid-conjugation/, 2, pages (first available 2015) (Year: 2015).

Pratap Kumar et al., "Gonadotropin-releasing hormone analogs: Understanding advantages and limitations"; Journal of Human Reproductive Sciences, 7(3):170-174 (2014) (Year: 2014).

Esben Bech et al., "Chemical Strategies for Half-Life Extension of Biopharmaceuticals: Lipidation and Its Alternatives"; ACS Medicinal Chemistry Letters; 9:577-580 (2018) (Year: 2018).

Office Action dated Apr. 5, 2022 issued by the Russian Patent Office in Russian Application No. 2020142694/10.

Communication dated Sep. 18, 2023, issued in Chinese Application No. 201980054022.7.

Wang Qiao et al., "Research on peptide and protein drug delivery systems", Institute of Materia Medica, Xinjiang Academy of Medical Sciences, Taozhou 310013, 1992, vol. 24, pp. 16-18 (8 pages total).

\* cited by examiner

LONG-ACTING FATTY ACID-CONJUGATED GnRH DERIVATIVES AND PHARMACEUTICAL COMPOSITIONS CONTAINING SAME This application is a Rule 53(b) Divisional of U.S. application Ser. No. 17/075,295 filed Oct. 20, 2020, which is a Continuation Application of PCT International Application No. PCT/KR2019/003527, filed on Mar. 26, 2019, the entire contents of which are incorporated herein by reference in their entirety.

TECHNICAL FIELD

The present disclosure relates to novel long-acting fatty acid-conjugated derivatives of gonadotrophin-releasing hormone (GnRH) and pharmaceutical compositions containing the same.

BACKGROUND

In general, a gonadotrophin-releasing hormone (GnRH) or a luteinizing hormone-releasing hormone is a hypothalamic neurohormone and is a type of neuroendocrine peptide. Specifically, GnRH is synthesized in the neurovascular terminal cells of the hypothalamus and acts on gonadotropic cells in the anterior pituitary gland to promote the synthesis and release of luteinizing hormone (LH) or follicle stimulating hormone (FSH), which are both gonadotrophins. Luteinizing hormones or follicle stimulating hormones, the synthesis and release of which are controlled by GnRH, play a role in controlling male and female sex hormones and maturing reproductive cells.

It is known that, while GnRH has the effect of promoting the secretion of gonadotropin or ovulation at normal concentrations, it has an antagonistic inhibitory effect at high concentrations, which is contradictory. A high dose of GnRH may be used to treat prostate cancer or breast cancer, which are hormone-dependent tumors, as well as endometriosis, uterine fibroids, central precocious puberty, and adenomyosis, etc. It is also widely known that GnRH or GnRH derivatives can be used in the treatment of various sex hormone-dependent diseases (Kumar P. and Sharma A, J Hum Reprod Sci, 2014; 7(3): pp. 170-174).

As for commercially available therapeutic agents comprising GnRH, there exist sustained release products designed to be injected every one or three months, which are in the form of a biodegradable multinuclear storage microcapsules (PLGA or PLA) containing a GnRH agonist. Particularly, a sustained-release product comprising a GnRH derivative under the brand name of Lupron® Depot is commercially available. This commercial product contains PLGA [poly(lactic-co-glycolic acid)] microspheres as a sustained release ingredient, with the GnRH derivative of leuprolide acetate as an active ingredient. Due to the use of a biodegradable polymer, Lupron® Depot must be intramuscularly or subcutaneously administered at a large dose. In this regard, pain or tissue injury is accompanied at the injection site and a lump remains at the site for several months, with the occasional incidence of inflammation, since the biodegradable polymers are not completely absorbed even after one month. For Lupron® Depot, these drawbacks are attributed to the fact that the biodegradable polymer is added after being physically mixed with the GnRH derivative. When the biodegradable polymer is physically mixed with the GnRH derivative, the GnRH derivative is surrounded with layers of the biodegradable polymer. With the degradation of the biodegradable polymer surrounding the GnRH derivative in vivo, the GnRH derivative is released, presenting a pharmacological effect. Meanwhile, because the biodegradable polymer is mixed physically, there is a side effect in that the biodegradable polymer remains for a long time in vivo during the degradation.

In order to overcome these drawbacks of Lupron® Depot, although other products including Eligard® have been additionally developed, they are still disadvantageous in terms of the initial drug release, low drug stability in the mixed solution phase, etc. There is thus a continuing need to develop formulations or dosage forms which allow high blood levels of GnRH to be maintained for a prolonged period of time.

Existing GnRH sustained-release products, which are intended to slowly release GnRH into blood, contain additional sustained release ingredients for releasing the active ingredient over a prolonged period of time. Accordingly, the total dose of the products increases, which leads to problems of pain, residual feeling at the injection site, low drug stability, etc. Particularly, among the patients who had received the existing products (leuprolide acetate), as much as 23 to 30% of the patients complained about pain at the injection sites (Lee P A et al., J. Clin, Endocrinol Metab, 2014).

Meanwhile, U.S. Pat. No. 9,694,051 discloses that a conjugated adrenomedullin peptide where an alkyl moiety is conjugated to lysine (Lys) at the N-terminals of some adrenomedullin peptides has an increased half-life in blood. Although an increase in the half-life in blood of the peptide is exhibited by conjugating an alkyl moiety to the N-terminal of the peptide, the peptide is quite different from GnRH in terms of function and sequence. Also, the peptide differs from GnRH in that the terminal amino residue of the peptide to which the alkyl moiety is conjugated is lysine.

Under such circumstances, the present inventor has made efforts to develop a long-acting GnRH formulation in which the GnRH itself has a prolonged in vivo half-life and increased bioavailability, unlike the existing sustained-release formulations which have disadvantages due to the additional ingredients or formulation design for sustained release, etc. Specifically, a long-acting fatty acid-conjugated GnRH derivative was prepared by conjugating a fatty acid to a GnRH derivative which is designed to have an increased in vivo half-life of GnRH and converting the conjugate to a salt form. The long-acting fatty acid-conjugated GnRH derivative was found to exhibit excellent bioavailability and a prolonged in vivo half-life, maintain a high blood level, and have a therapeutic effect on sex hormone-dependent diseases or deter sexual maturation, which led to the present disclosure.

The long-acting fatty acid-conjugated GnRH derivatives according to the present disclosure and a pharmaceutical composition containing the same can be used for the prevention and treatment of various sex hormone-dependent diseases or for the deterrence of sexual maturation.

SUMMARY

In consideration of the above problems with the existing sustained release formulations, the present disclosure aims to develop a long-acting GnRH formulation having increased bioavailability and in vivo half-life of GnRH itself, which is as short as 2 to 4 min in circulating blood. Thus, the purpose of the present disclosure is to provide a long-acting fatty acid-conjugated GnRH derivative with ease of administration and improved efficacy and a pharmaceutical composition containing the same.

Leading to the present disclosure, painstaking research, conducted by the present inventor, into a GnRH derivative with an increased bioavailability and in vivo half-life of GnRH itself, which has a circulating half-life of as short as 2 to 4 min in the natural form, resulted in the finding that a long-acting fatty acid-conjugated GnRH derivative, which is a GnRH derivative having a fatty acid conjugated thereto, and a pharmaceutically acceptable salt thereof have an improved efficacy and in vivo half-life.

As used herein, the term "improved efficacy" of a long-acting fatty acid-conjugated GnRH derivative means that it has a higher therapeutic effect on sex hormone-related diseases at the same concentration with a natural GnRH. For example, it means that the long-acting fatty-conjugated GnRH derivative has higher cytotoxic effects on prostate cancer or breast cancer when administered at the same dose as a natural GnRH or a commercially available GnRH derivative.

GnRH has the effect of promoting the release of gonadotropins or ovulation at normal concentrations, while it has antagonistic inhibitory effects at high concentrations which is contradictory. Accordingly, high concentrations of GnRH inhibit the progression of diseases aggravated by sex hormones or are effective for the alleviation and treatment of sex hormone-dependent diseases.

Hereinafter, a detailed description will be provided with respect to the GnRH derivative; the long-acting fatty acid-conjugated GnRH derivative, which comprises a GnRH derivative having a fatty acid conjugated thereto, or a pharmaceutically acceptable salt thereof; and a pharmaceutical composition containing the same according to the present disclosure.

1. Long-Acting, Fatty Acid-Conjugated GnRH Derivatives

An aspect of the present disclosure pertains to a long-acting, fatty acid-conjugated GnRH derivative, which is a gonadotropin-releasing hormone (GnRH) derivative having a fatty acid conjugated thereto, or a pharmaceutically acceptable salt thereof.

As used herein, the term "Gonadotropin-releasing hormone (GnRH)" refers to a hormone synthesized in the neurovascular terminal cells of the hypothalamus and acts on gonadotropic cells in the anterior pituitary gland to promote the synthesis and release of a luteinizing hormone (LH) or a follicle stimulating hormone (FSH), which are both gonadotrophins. GnRH may differ in sequence from one species to another. Mammalian natural GnRH may have the amino acid sequence of SEQ ID NO: 1 as follows.

```
[Mammalian GnRH sequence]
                                    (SEQ ID NO: 1)
   pGlu-His-Trp-Ser-Tyr-Gly-Leu-Arg-Pro-Gly
```

As used herein, the term "GnRH derivative" refers to a substance which is structurally analogous to GnRH, but may act in a different manner in vivo. At an early stage after being administered, the GnRH derivative, particularly corresponding to a GnRH agonist, binds to a GnRH receptor to promote the in vivo synthesis and secretion of follicle stimulation hormone (FSH) and luteinizing hormone (LH) to a certain level. However, the continuous maintenance of the GnRH derivative concentration in vivo depletes gonadotropins and downregulates the GnRH receptor, resulting in a contradictory effect (i.e., antagonistic effect) in that the synthesis and secretion of FSH and LH are rather suppressed. Through such effects, the GnRH derivatives can thus be used for preventing or treating sex hormone-dependent diseases and for deterring sexual maturation.

In one embodiment of the present disclosure, the GnRH derivative is a GnRH agonist, which may be selected from the group consisting of leuprolide, goserelin, triptorelin, nafarelin, buserelin, histrelin, deslorelin, meterelin, gonadorelin, and modified derivatives thereof.

In another embodiment of the present disclosure, the GnRH derivative has a sequence that has at least 80%, at least 85%, at least 90%, at least 95%, or at least 98% homology to the existing GnRH agonists.

Particularly, the GnRH derivative of the present disclosure may have a sequence that has at least 80%, at least 85%, at least 90%, at least 95%, or at least 98% homology to natural GnRH, leuprolide, goserelin, triptorelin, nafarelin, buserelin, histrelin, deslorelin, meterelin, or gonadorelin and, more particularly, a sequence that has at least 80%, at least 85%, at least 90%, at least 95%, or at least 98% homology to GnRH (SEQ ID NO: 1) or leuprolide (SEQ ID NO: 2).

In an embodiment of the present disclosure, a GnRH derivative is a modified leuprolide where the first amino acid, glutamic acid, on leuprolide is substituted with a different amino acid, more particularly with glutamine.

In an embodiment of the present disclosure, the GnRH derivative may include or consist of an amino acid sequence selected from the group consisting of SEQ ID NOS: 2 to 11. In an embodiment of the present disclosure, the long-acting fatty acid-conjugated GnRH derivative may include or consist of an amino acid sequence selected from the group consisting of SEQ ID NOS: 4 to 11. In an embodiment of the present disclosure, the long-acting fatty acid-conjugated GnRH derivative may include or consists of an amino acid sequence of SEQ ID NO: 5 or 11.

In an embodiment of the present disclosure, the GnRH derivative may mean a derivative having an additional modification of the existing GnRH or GnRH derivative.

Specifically, the GnRH derivative according to an embodiment of the present disclosure may be a long-acting fatty acid-conjugated GnRH derivative, which is a GnRH derivative having a fatty acid conjugated thereto, or a pharmaceutically acceptable salt thereof. More particularly, the fatty acid may be conjugated to the amino terminus of the GnRH derivative.

In an embodiment of the present disclosure, the fatty acid may be a saturated or unsaturated fatty acid of C6 to C30, which may be linear or branched. In an embodiment of the present disclosure, concrete examples of the fatty acid include, but are not limited to, caproic acid, enanthic acid, caprylic acid, pelargonic acid, capric acid, undecylic acid, lauric acid, myristic acid, palmitic acid, stearic acid, arachidic acid, behenic acid, lignoceric acid, cerotic acid, myristoleic acid, palmitoleic acid, linolenic acid, alpha-linolenic acid (ALA), eicosapentaenoic acid, (EPA), docosahexaenoic acid (DHA), linoleic acid (LA), gamma-linoleic acid (GLA), dihomo gamma-linoleic acid (DGLA), arachidonic acid (AA), oleic acid, vaccenic acid, elaidic acid, eicosanoic acid, erucic acid, and nervonic acid. So long as it achieves the purpose of the present disclosure, any fatty acid may be employed, without limitations. Lauric acid, also systemically called dodecanoic acid, is a saturated fatty acid with a normal 12-carbon atom chain and exists as a component of triglycerides. It is structurally stable and is found as one of the main components in human breast milk. The fatty acid has a melting point of 43.8° C. and exists as a white solid at room temperature.

As used herein, the term "palmitic acid" refers to a carboxyl of a hydrocarbon chain which is a hydrophobic normal saturated fatty acid of 16 carbon atoms and has one carboxyl group (—COOH).

As used herein, the term "arachidic acid" or "eicosanoic acid" is a saturated fatty acid with a normal 20-carbon chain. It has a melting point of 75.5° C. and exists as a white crystalline solid at room temperature.

Through the conjugation with palmitic acid, the long-acting GnRH derivative according to an embodiment of the present disclosure has the following advantages: i) enhanced renal reabsorption and fat storage efficiency; ii) protection effect resulting from increased binding with serum proteins; iii) delayed renal clearance resulting from increased hydrophobicity of analog series; and iv) increase in release time and pharmaceutical efficacy resulting from attaching to lipid membranes or biological membranes.

An emulsion of dexamethasone palmitate where palmitic acid is conjugated to dexamethasone is known to exhibit an anti-inflammatory effect 5.6-fold higher than dexamethasone alone at the same dose (Peng et al., Drug Development and Industrial Pharmacy, 2010: 36(12)). Commercially available, long-acting products which are formulated by fatty acid conjugation are exemplified by INVEGA TRINZA® where paliperidone is conjugated with a fatty acid and Lipotalon® where dexamethasone is conjugated with a fatty acid.

It is known that when a palmitic acid is conjugated to hormones or enzymes, the in vivo half-life of the hormones or enzymes is increased due to the above mechanism. However, their water solubility may be significantly decreased due to the increased hydrophobicity of the molecule. Further, intermolecular aggregation in a water-soluble environment or intramolecular hydrophobic bonds at hydrophobic sites of the protein may be caused. Hence, when conjugated with a fatty acid such as palmitic acid, proteins may suffer from the disadvantage of decreases in stability of the formulation, bioavailability, and protein activity.

In this regard, there is a need for an appropriate formulation strategy for increasing the in vivo half-life of proteins through conjugation with a fatty acid, without decreasing the efficacy of the specific protein or causing protein aggregation.

As used herein, a "pharmaceutically acceptable salt" is intended to encompass all pharmaceutically acceptable salts that can be used for the purpose of increasing the stability, water solubility, bioavailability, etc., of the fatty acid-conjugated GnRH derivative according to an embodiment of the present disclosure, without limitations thereto.

In one embodiment of the present disclosure, the pharmaceutically acceptable salt may be selected from the group consisting of inorganic acids, organic acids, ammonium salts, alkali metal salts, and alkaline earth metal salts. In another embodiment, the pharmaceutically acceptable salt may be selected from the group consisting of hydrochloride, hydrobromide, phosphate, metaphosphate, nitrate, sulfate, acetate, sulfonate, benzoate, citrate, ethanesulfonate, fumarate, lactate, maleate, malate, succinate, tartrate, sodium salt, calcium salt, potassium salt, and magnesium salt.

In one embodiment of the present disclosure, the fatty acid-conjugated GnRH derivative of the present disclosure may include or may be composed of an amino acid selected from the group consisting of SEQ ID NOS: 4 to 11, wherein lauric acid, palmitic acid, or arachidic acid may be conjugated to the amino terminus of the GnRH derivative, and the pharmaceutically acceptable salt may be a sodium salt or acetate.

In another embodiment of the present disclosure, the fatty acid-conjugated GnRH derivative may include or may be composed of the amino acid sequence of SEQ ID NO: 3 or 4, wherein lauric acid may be conjugated to the amino terminus of the GnRH derivative, and the pharmaceutically acceptable salt may be an acetate.

In a further embodiment of the present disclosure, the palmitic acid-conjugated GnRH derivative may include or may be composed of the amino acid sequence of SEQ ID NO: 9 or 10, wherein arachidic acid may be conjugated to the amino terminus of the GnRH derivative, and the pharmaceutically acceptable salt may be an acetate.

2. Pharmaceutical Compositions Comprising the Fatty Acid-Conjugated GnRH Derivative An aspect of the present disclosure pertains to a pharmaceutical composition comprising the long-acting, fatty acid-conjugated GnRH derivative according to an embodiment of the present disclosure as an active ingredient.

In an embodiment of the present disclosure, the pharmaceutical composition may further comprise a cyclodextrin. In this regard, the cyclodextrin may be α-cyclodextrin, β-cyclodextrin, or γ-cyclodextrin and may be particularly methyl-β-cyclodextrin. However, so long as it achieves the purpose of the present disclosure, any cyclodextrin may be used.

In an embodiment of the present disclosure, the long-acting fatty acid-conjugated GnRH derivative may exist as being included within a cyclodextrin. In this regard, the fatty acid-conjugated GnRH derivative and cyclodextrin can form an inclusion complex.

In an embodiment of the present disclosure, a cyclodextrin can form an inclusion complex with an active ingredient that is difficult to dissolve in water, thereby providing the water-insoluble ingredient with stability, improved solubility, and sustainable release in an aqueous solution. Therefore, in an embodiment of the present disclosure, the pharmaceutical composition comprising an inclusion complex of the long-acting fatty acid-conjugated GnRH derivative and a cyclodextrin can exhibit improved sustainability of release of the GnRH derivative.

In the present disclosure, a cyclodextrin is a non-reducing cyclic oligosaccharide consisting of a macrocyclic ring of glucose subunits $(C_6H_{10}O_5)_n$ joined by α-1,4 glycosidic bonds, called α-cyclodextrin, β-cyclodextrin, and γ-cyclodextrin for n=6, 7, and 8, respectively.

In an embodiment of the present disclosure, the pharmaceutical composition may contain a cyclodextrin and the active ingredient long-acting fatty acid-conjugated GnRH derivative at a molar ratio of from about 7:1 to 1:1, from 6:1 to 1:1, or from 5:1 to 1:1. At such weight ratios, the pharmaceutical composition according to an embodiment of the present disclosure can exhibit excellent solubility.

In an embodiment of the present disclosure, the pharmaceutical composition comprises a pharmaceutically effective amount of the fatty acid-conjugated GnRH derivative according to an embodiment of the present disclosure and may further comprise a pharmaceutically acceptable carrier. As used herein, the term "pharmaceutically effective amount" means a sufficient amount to achieve the efficacy or activity of the fatty acid-conjugated GnRH derivative according to an embodiment of the present disclosure.

Pharmaceutically acceptable carriers which can be included in the pharmaceutical composition according to an embodiment of the present disclosure are those commonly used for preparing a formulation, and examples of the pharmaceutically acceptable carrier include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil, but are not limited thereto.

In addition to the above ingredients, the pharmaceutical composition according to an embodiment of the present disclosure may further comprise a lubricant, a humectant, a sweetener, a flavorant, an emulsifier, a suspending agent, a preservative, and the like.

In an embodiment of the present disclosure, the pharmaceutical composition may be administered orally or parenterally. Particularly, for injection routes, it may be administered in a dosage form of either a subcutaneous injection or an intramuscular injection. A dosage form may be selected in consideration of various factors, such as the effect of controlling in vivo concentrations.

In an embodiment of the present disclosure, the pharmaceutical composition of the present disclosure may be administered in the dosage form of an injection, a paste, a gelling agent, a lotion, a capsule, a tablet, a liquid, a suspension, a sprayer, an inhaler, an eye drop, an adhesive, or a patch and particularly an injection.

In an embodiment of the present disclosure, the suitable dosage of the pharmaceutical composition varies depending on factors including the formulation method, dosing method, patient's age, body weight, gender and morbidity, food, administration time, administration route, excretion rate, and response sensitivity. The pharmaceutical composition of the present disclosure is generally administered at a dose of 0.001 to 100 mg/kg for an adult. The pharmaceutical composition comprises the fatty acid-conjugated GnRH derivative according to an embodiment of the present disclosure in an amount of about 0.001 to 30 mg/mL.

In an embodiment of the present disclosure, the term "about" is intended to cover an allowable error for a process or a numerical adjustment falling within the technical spirit of the present disclosure. For instance, the term "about" refers to a relative term denoting an approximation of ±10% of the nominal value to which it refers, in one embodiment, to ±5%, and in another embodiment, to ±2%. For the field of this disclosure, this level of approximation is appropriate unless the value is specifically stated to require a tighter range.

In an embodiment of the present disclosure, the pharmaceutical composition is formulated using a pharmaceutically acceptable carrier and/or excipient, according to a method that can be easily carried out by a person having ordinary skill in the art. The pharmaceutical composition of the present disclosure may be prepared into a unit dosage form or may be inserted into a multi-dose container. In this regard, the formulation may be in the form of a solution, a suspension, a syrup, or an emulsion in an oil or aqueous medium or in the form of an extract, powder, granules, a tablet, or a capsule and may further comprise a dispersant or a stabilizer.

In an embodiment of the present disclosure, the pharmaceutical composition may be used for the prevention or treatment of a sex hormone-dependent disease or for deterrence of sexual maturation. The sex hormone-dependent disease may be selected from the group consisting of prostate cancer, breast cancer, ovarian cancer, endometriosis, uterine fibroid, polycystic ovary disease, central precocious puberty, hypertrichosis, gonadotroph pituitary adenoma, sleep apnea, irritable bowel syndrome, premenstrual syndrome, benign prostatic hyperplasia, and contraception, but is not limited thereto.

In an embodiment of the present disclosure, when used in combination with a conventional biodegradable polymer, the pharmaceutical composition may exhibit a remarkably excellent in vivo half-life. Accordingly, the pharmaceutical composition according to an embodiment of the present disclosure may further comprise biodegradable polymers.

In an embodiment of the present disclosure, the biodegradable polymer allows the drug to be delivered to parenteral routes through the body, or allows the polymer comprising the GnRH derivative of the present disclosure or a salt thereof to topically act on a specific site. With respect to the biodegradable polymer in the present disclosure, reference may be made to Chasin M et al. ("Biodegradable Polymers as Drug Delivery Systems", New York, Marcel Dekker, 1990) or D. Wescman et al. ("Handbook of Biodegradable Polymers", Taylor & Francis, 1998), without limitations thereto.

By way of example, the biodegradable polymer according to an embodiment of the present disclosure may be PLA (poly-lactic acid), linear or branched PLGA (poly(lactic-co-glycolic acid)), PGA (poly-glycolic acid), hydrogel, or the like.

According to an aspect thereof, the present disclosure further provides a method and use for deterring sexual maturation or a method and use for preventing or treating a sex hormone-related symptom or disease by administering the palmitic acid-conjugated GnRH derivative according to an embodiment of the present disclosure, a salt thereof, or a composition containing the same to mammals including humans.

An aspect of the present disclosure pertains to a use of the fatty acid-conjugate GnRH derivative or a salt thereof according to an embodiment of the present disclosure in deterring sexual maturation or in preventing or treating a sex hormone-related symptom or disease.

An aspect of the present disclosure pertains to a pharmaceutical composition for use in deterring sexual maturation or in preventing or treating a sex hormone-related symptom or disease, the composition comprising the fatty acid-conjugated GnRH derivative according to an embodiment of the present disclosure, a salt thereof, or both of them.

An aspect of the present disclosure pertains to a use of the fatty acid-conjugated GnRH derivative according to an embodiment of the present disclosure or a salt thereof in preparing a pharmaceutical composition (or medicament) for deterring sexual maturation or for preventing or treating a sex hormone-related symptom or disease.

The excellent bioavailability and extended in vivo half-life by the novel long-acting fatty acid-conjugated gonadotrophin-releasing hormone (GnRH) derivative according to an embodiment of the present disclosure is expected to make great contributions to the reduction in dosing frequency and dosage. Particularly, the long-acting fatty acid-conjugated GnRH derivative could overcome the problems with the existing sustained release GnRH formulations, such as the adverse effects of residual feeling and pain at the injection site.

In addition, the long-acting fatty acid-conjugated GnRH derivative and the pharmaceutical composition comprising the same according to an embodiment of the present disclosure exhibit remarkably excellent therapeutic effects on sex hormone-dependent diseases and as such, are expected to make great contributions to the reduction in dosing frequency and dosage.

DETAILED DESCRIPTION

Figure 1:
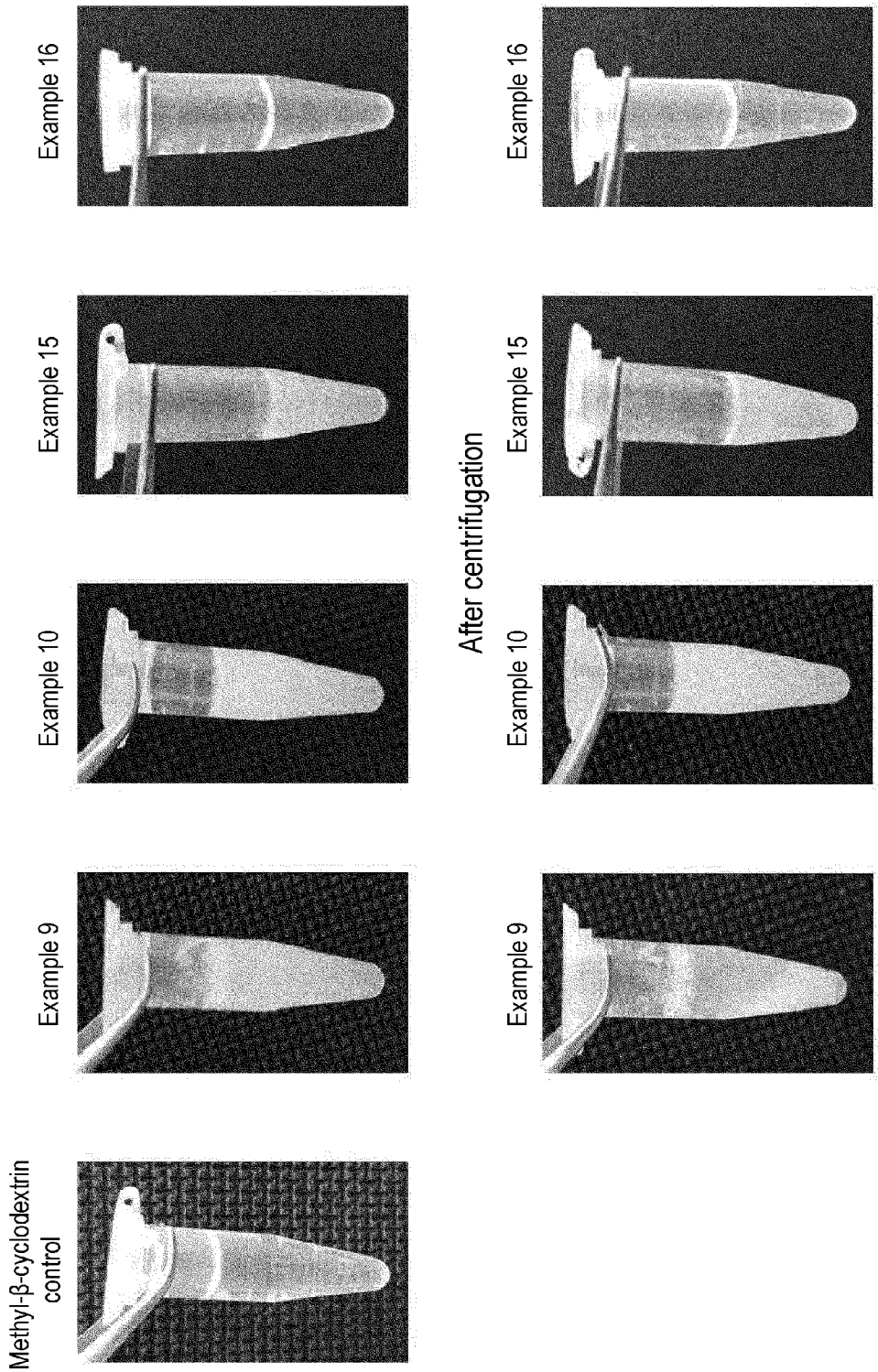
FIG. 1 shows images in which the extents of suspensions formed by pharmaceutical compositions (Examples, 9, 10, 15, and 16) comprising fatty acid-conjugated GnRH derivatives (Examples 1, 2, 7, and 8) according to an embodiment of the present disclosure and cyclodextrin are visualized with the naked eye.

Hereinafter, the embodiments of the present disclosure will be described by referring to the Preparation Examples and Examples, which are set forth to illustrate the present disclosure, but not construed to limit the present invention.

Preparation Example 1: Preparation of Gonadotrophin-Releasing Hormone (GnRH) Derivatives Natural mammalian GnRH has the following sequence.

```
[Mammalian GnRH Sequence]
                                        (SEQ ID NO: 1)
    pGlu-His-Trp-Ser-Tyr-Gly-Leu-Arg-Pro-Gly
```

Leuprolide® having the mammalian GnRH sequence with the substituted D-Leu instead of Gly at position 6 and the substituted des-Gly instead of Gly at position 10 was used as a backbone for the derivative and the fatty acid-conjugate derivative according to an embodiment of the present disclosure.

```
[Leuprolide Sequence]
                                        (SEQ ID NO: 2)
    pGlu-His-Trp-Ser-Tyr-D-Leu-Leu-Arg-Pro-NHEt
```

Derivatives where glutamate at position 1 on the Leuprolide sequence remains unsubstituted or was substituted with glutamine were prepared as follows.

For reference, the sequence of triptorelin is provided as follows:

```
[Triptorelin Sequence]
                                        (SEQ ID NO: 3)
    pGlu-His-Trp-Ser-Tyr-D-Trp-Leu-Arg-Pro-Gly-NH2
```

(1) Preparation Method for GnRH Derivative Peptides

The derivatives are synthesized using a general Fmoc/tBu solid-phase peptide synthesis (SPPS) method, where the α-amino groups of amino acid residues are protected by the base-labile group of Fmoc (fluorenylmethyloxycarbonyl chloride) while the side groups are protected by an acid-labile group. In the solid phase peptide synthesis method comprising the following steps, a peptide chain is sequentially extended by repetitive Fmoc cleavage and amino acid coupling.

① Load Fmoc amino acid onto resin (Fmoc-Pro-trityl resin);
② Remove Fmoc protecting group from Fmoc-AA-resin (20% piperidine/DMF);
③ Wash with DMF;
④ Bind amino acid after activation (DIC/HOBt used);
⑤ Wash with DMF;
⑥ Repeat steps 2 to 0 to bind amino acids sequentially;
⑦ Remove resin only from synthesized peptide (1.5% TFA/DCM);
⑧ Attach ethylamine to the amino terminus of the resulting peptide (using EDC-HCl/HOAt); and
⑨ Make overall cleavage of protected side chains from the resulting peptide (92.5% TFA/2.5% TIS/2.5% EDT/2.5% H2O).

According to the preparation method above, derivatives having the sequences described in Table 2 were prepared. Lauric acid, palmitic acid, or arachidic acid was conjugated to the amino terminus of the obtained GnRH derivative, as instructed in Table 2. Conjugating a fatty acid to the amino terminus of the derivative was carried out in the same manner as the conjugation of general amino acids. The synthesis of the GnRH derivatives of the Comparative Examples and Examples was entrusted to Anygen Co. Ltd.

(2) Purification of GnRH Derivative Peptides

Following the TFA cleavage, the peptide was purified using a C18 column in the Shimadzu HPLC 10AVP system under HPLC conditions (A buffer 0.05% TFA/H$_2$O, B buffer 0.05% TFA/acetonitrile, flow rate 1 mL/min, wavelength 230 nm). Purification results in each Example were entrusted to and obtained from Anygen Co. Ltd. and are shown in Table 1. In Table 1, the GnRH derivatives of Example 1 (L1), Example 3 (P1), Example 5 (P3), and Example 7 (A1) have glutamate as the amino acid residue at position 1, while the GnRH derivatives of Example 2 (L2), Example 4 (P2), Example 6 (P4), and Example 8 (A2) have glutamine as the amino acid residue at position 1 (see Table 2).

temperature with respective melting points of about 43.8° C., about 60° C., and about 75.5° C. Hence, as the fatty acid-conjugated GnRH derivatives might be poorly soluble in water, salting was further carried out. The fatty acid-conjugated GnRH derivatives were subjected to salting with sodium salt or acetate to prepare the fatty acid-conjugated GnRH derivative salts of Comparative Examples 1 to 3 and Examples 1 to 8, as shown in Table 2 below. These processes were entrusted to Anygen Co. Ltd.

TABLE 2

| Derivative | Backbone/Derivative Sequence and Salt |
|---|---|
| Comparative Example 1 (GnRH) | pyroGlu-His-Trp-Ser-Tyr-Gly-Leu-Arg-Pro-Gly-NH$_2$ acetate salt (SEQ ID NO: 1) |
| Comparative Example 2 (Leuprolide) | pyroGlu-His-Trp-Ser-Tyr-D-Leu-Leu-Arg-Pro-NHEt acetate salt (SEQ ID NO: 2) |
| Comparative Example 3 (Triptorelin) | pyroGlu-His-Trp-Ser-Tyr-D-Trp-Leu-Arg-Pro-Gly-NH$_2$ acetate salt (SEQ ID NO: 3) |
| Example 1 | Lauric acid-Glu-His-Trp-Ser-Tyr-D-Leu-Leu-Arg-Pro-NHEt acetate salt (SEQ ID NO: 4) |
| Example 2 | Lauric acid-Gln-His-Trp-Ser-Tyr-D-Leu-Leu-Arg-Pro-NHEt acetate salt (SEQ ID NO: 5) |
| Example 3 | Palmitic acid-Glu-His-Trp-Ser-Tyr-D-Leu-Leu-Arg-Pro-NHEt sodium salt (SEQ ID NO: 6) |
| Example 4 | Palmitic acid-Gln-His-Trp-Ser-Tyr-D-Leu-Leu-Arg-Pro-NHEt sodium salt (SEQ ID NO: 7) |
| Example 5 | Palmitic acid-Glu-His-Trp-Ser-Tyr-D-Leu-Leu-Arg-Pro-NHEt acetate salt (SEQ ID NO: 8) |
| Example 6 | Palmitic acid-Gln-His-Trp-Ser-Tyr-D-Leu-Leu-Arg-Pro-NHEt acetate salt (SEQ ID NO: 9) |
| Example 7 | Arachidic acid-Glu-His-Trp-Ser-Tyr-D-Leu-Leu-Arg-Pro-NHEt acetate salt (SEQ ID NO: 10) |
| Example 8 | Arachidic acid-Gln-His-Trp-Ser-Tyr-D-Leu-Leu-Arg-Pro-NHEt acetate salt (SEQ ID NO: 11) |

TABLE 1

| GnRH Derivative | Purity (%) | MS Calc. (Da) | MS Found (Da) |
|---|---|---|---|
| Example 1(L1) | 98.4 | 1409.7 | 1409.6 |
| Example 2(L2) | 99.0 | 1408.7 | 1409.0 |
| Example 3(P1) | 98.2 | 1465.8 | 1465.7 |
| Example 4(P2) | 98.2 | 1464.8 | 1464.9 |
| Example 5(P3) | 98.1 | 1465.8 | 1465.5 |
| Example 6(P4) | 98.3 | 1464.8 | 1464.0 |
| Example 7(A1) | 98.9 | 1521.7 | 1521.1 |
| Example 8(A2) | 98.8 | 1520.7 | 1520.9 |

Lauric acid, palmitic acid, and arachidic acid are sparingly soluble in water and exist as solid phases at room Preparation Example 2: Preparation of Pharmaceutical Composition Comprising Inclusion Complex of GnRH Derivative and Cyclodextrin Methyl-β-cyclodextrin powder (SigmaAldrich; Lot no.: C4555; Mw.: 1303.311 g/mol) was dissolved in the amounts given in Table 3 in 1 mL of sterilized tertiary distilled water.

The GnRH derivatives were added in the amounts given in Table 3 to respective 15-mL conical tubes to which 1 mL of the aqueous β-cyclodextrin solution corresponding to the mole ratios of Table 3 was then added before mixing overnight at room temperature with the aid of a low-speed rotator. Subsequently, the solutions contained in the 15-mL tubes were collected by a brief spin down and then transferred to 1.5 mL tubes, followed by secondary mixing overnight at room temperature by a low-speed rotator. Finally, pharmaceutical compositions containing each the active ingredients at a concentration of about 10 mM were obtained. The compositions were used in the following Experimental Examples optionally after being diluted. For Comparative Examples 1 to 3, the compositions were diluted to 20 mM in tertiary distilled water.

TABLE 3

| | C. Example | | | 9 | 10 | 11 | EXAMPLE 12 Example | 13 | 14 | 15 | 16 |
|---|---|---|---|---|---|---|---|---|---|---|---|
| GnRH Derivative | 1 24 mg | 2 24 mg | 3 24 mg | 1 14 mg | 2 14 mg | 3 15 mg | 4 15 mg | 5 15 mg | 6 15 mg | 7 15 mg | 18 15 mg |
| Methyl-β-cyclodextrin | — | — | — | 13 mg | 13 mg | 13 mg | 65 mg | 13 mg | 65 mg | 13 mg | 13 mg |
| Mole ratio (cyclodextrin: GnRH Derivative) | — | — | — | 1:1 | 1:1 | 1:1 | 5:1 | 1:1 | 5:1 | 1:1 | 1:1 |

The following Experimental Examples were carried out with the pharmaceutical compositions.

Experimental Example Evaluation of Inclusion Complex of Fatty Acid-Conjugated GnRH Derivative and Cyclodextrin For use as a control, a solution of 13 mg of methyl-β-cyclodextrin powder in 1 mL of sterile, tertiary distilled water was prepared in the same manner as in Preparation Example 2 in a 1.5-mL tube (concentration 10 mM).

Figure 2:
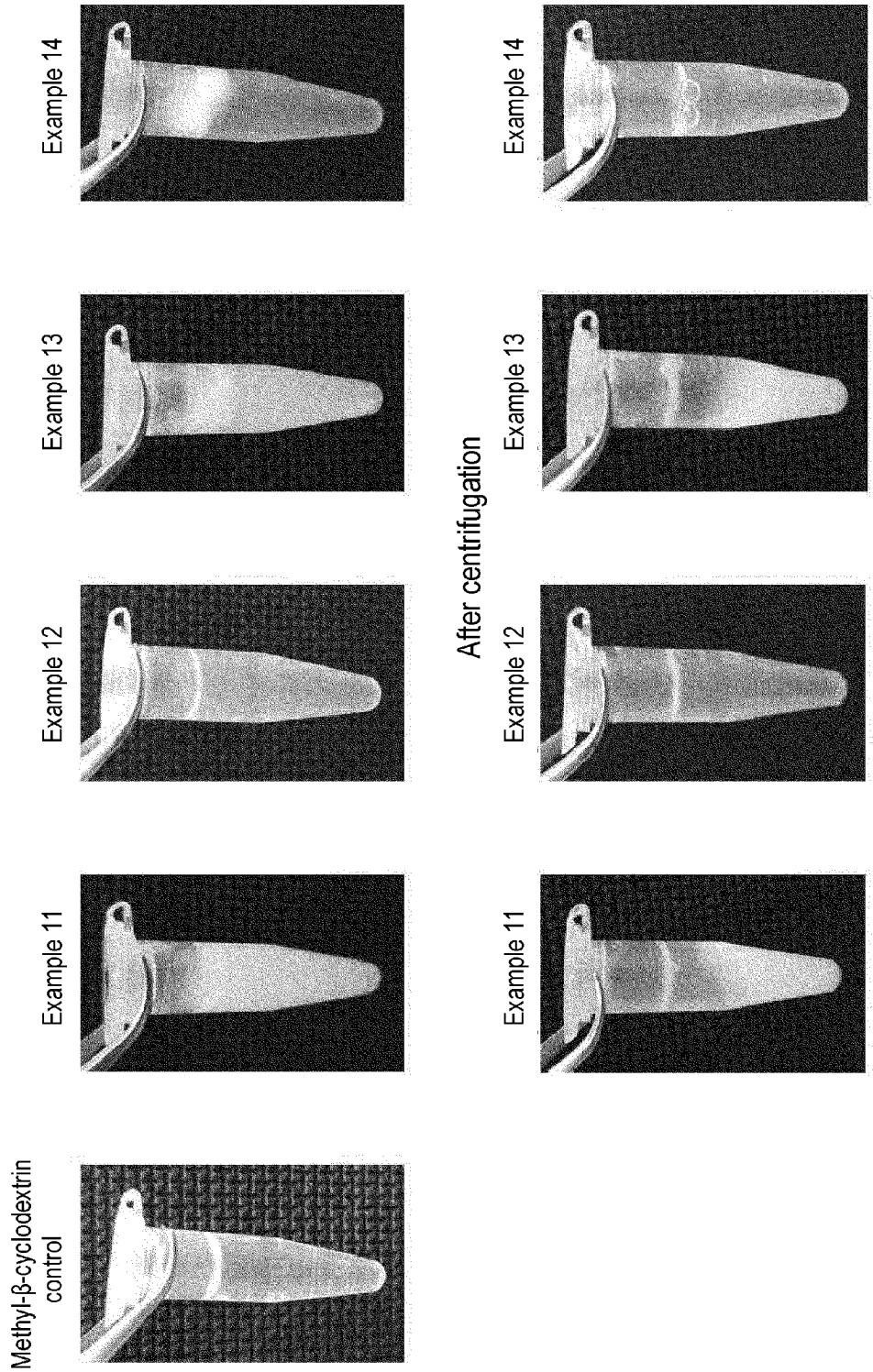
FIG. 2 shows images in which the extents of suspensions formed by pharmaceutical compositions (Examples 11 to 14) comprising fatty acid-conjugated GnRH derivatives (Examples 3 to 6) according to an embodiment of the present disclosure and cyclodextrin are visualized with the naked eye.

The prepared control, and the compositions of Examples 9 to 16 finally prepared by mixing in 1.5-mL tubes were observed with the naked eye. They were spun down at 10,000 rpm for 40 seconds to 50 seconds (less than 1 minute) and again observed with the naked eye to evaluate solubility. The results of Examples 9, 10, 15, and 16 are depicted in FIG. 1, and the results of Examples 11 to 14 are depicted in FIG. 2. As can be seen in FIG. 1, the compositions of Examples 9 and 10 containing the lauric acid-conjugated GnRH derivatives (Examples 1 and 2) and the compositions of Examples 15 and 16 containing the arachidic acid-conjugated GnRH derivatives (Examples 7 and 8) were observed to exist as suspensions in which the active ingredients (inclusion complexes of GnRH derivatives and cyclodextrin) were well dispersed in the solvent sterile distilled water before the spin-down. This phenomenon was also true of the compositions after the spin-down.

As shown in FIG. 2, the compositions of Examples 11 to 14 containing the palmitic acid-conjugated GnRH derivatives (Examples 3 to 6) were also observed to exist as suspensions in which the active ingredients (inclusion complexes of GnRH derivatives and cyclodextrin) were well dispersed in the solvent sterile distilled water before and after the spin-down.

As implied by the results, the pharmaceutical compositions containing GnRH derivatives and cyclodextrin according to an embodiment of the present invention exist as suspensions in which the ingredients are well suspended, thus achieving the effects and purposes of long-acting or sustained released agents.

Experimental Example 2 Assay for Viability of Prostate Cancer Cell Lines

GnRH derivatives are clinically applied to the therapy of diseases including breast cancer, prostate cancer, endometriosis, central precocious puberty, and the like. Hence, different prostate cancer cell lines (DU-145, PC3, and LNCaP cell lines) were each cultured in an RPMI 1640 medium (containing 10% FBS, penicillin/streptomycin, 1% non-essential amino acids) in a T75 flask and cultured at 37° C. under the atmosphere of 5% C02/95% air in a sterile incubator. An assay for cell viability was performed using the Cell Counting Kit-8 (CCK-8, manufactured by DOJINDO). Each of the cell lines was separated from the T75 flask by trypsinization and transferred to 96-well plates at a density of 1×104 cells/mL for DU-145 and at a density of 1×105 cells/mL for PC3 and LNCaP, followed by incubation for one hour for attachment.

Subsequently, each cell line was treated with 100 μM and 200 μM of each of the derivatives of Comparative Examples 1 to 3 and Examples 9 to 16 and the control. In brief, 1% methyl β-cyclodextrin was used as a negative control for cell viability while 0.1% sodium dodecyl sulfate (SDS) served as a positive control. After 48 hours of incubation, the existing culture medium was removed, and 100 μL of fresh culture medium and 10 μL of CCK-8 solution were applied to each cell line. Again, after 48 hours of incubation, the medium solution was replaced by 100 μL of fresh culture medium and 10 μL of CCK-8 solution. The cells were incubated for 4 hours, and then the absorbance was measured at 450 nm to assess cell viability. The measurement results are provided in Tables 4 to 6 and FIGS. 3 to 5.

TABLE 4

| Derivative | Treatment conc. (μM) | Viability of DU-145 relative to negative control 1% methyl-β-cyclodextrin (%) | Statistical significance |
|---|---|---|---|
| Example 9 | 100 | 50.00 ± 0.63 | <0.01 |
| | 200 | 30.80 ± 0.66 | <0.01 |
| Example 10 | 100 | 36.40 ± 6.64 | <0.01 |
| | 200 | 25.40 ± 3.96 | <0.01 |
| Example 11 | 100 | 47.25 ± 2.50 | <0.02 |
| | 200 | 35.25 ± 0.25 | <0.01 |
| Example 12 | 100 | 36.75 ± 1.11 | <0.01 |
| | 200 | 33.50 ± 0.50 | <0.01 |
| Example 13 | 100 | 81.50 ± 1.44 | <0.01 |
| | 200 | 41.75 ± 1.18 | <0.01 |
| Example 14 | 100 | 38.50 ± 0.29 | <0.01 |
| | 200 | 32.00 ± 0.71 | <0.01 |
| Example 15 | 100 | 68.25 ± 0.95 | <0.01 |
| | 200 | 51.25 ± 2.95 | <0.01 |
| Example 16 | 100 | 50.25 ± 3.35 | <0.01 |
| | 200 | 39.00 ± 2.27 | <0.01 |
| C. Example 1 | 100 | 107.50 ± 2.56 | not significant (N.S) |
| | 200 | 101.08 ± 3.26 | N.S |
| C. Example 2 | 100 | 99.42 ± 2.06 | N.S |
| | 200 | 100.17 ± 3.07 | N.S |
| C. Example 3 | 100 | 100.92 ± 2.98 | N.S |
| | 200 | 94.27 ± 3.47 | N.S |
| Positive Control (0.1% SDS) | | 18.18 ± 2.32 | <0.01 |

TABLE 5

| Derivative | Treatment conc. (μM) | Viability of PC3 relative to negative control 1% methyl-β-cyclodextrin (%) | Statistical significance |
|---|---|---|---|
| Example 9 | 100 | 41.00 ± 4.36 | <0.02 |
| | 200 | 39.00 ± 4.73 | <0.02 |
| Example 10 | 100 | 41.00 ± 1.53 | <0.02 |
| | 200 | 23.00 ± 5.51 | <0.02 |
| Example 11 | 100 | 65.60 ± 1.69 | <0.01 |
| | 200 | 29.80 ± 2.54 | <0.01 |
| Example 12 | 100 | 29.20 ± 3.04 | <0.01 |
| | 200 | 19.20 ± 1.93 | <0.01 |
| Example 13 | 100 | 99.60 ± 5.84 | N.S |
| | 200 | 104.60 ± 3.52 | N.S |
| Example 14 | 100 | 90.80 ± 4.04 | N.S |
| | 200 | 54.80 ± 3.93 | <0.01 |
| Example 15 | 100 | 72.50 ± 5.33 | <0.02 |
| | 200 | 63.75 ± 5.56 | <0.02 |
| Example 16 | 100 | 45.75 ± 5.41 | <0.02 |
| | 200 | 41.33 ± 3.38 | <0.02 |
| C. Example 1 | 100 | 105.44 ± 1.76 | N.S |
| | 200 | 100.11 ± 1.82 | N.S |
| C. Example 2 | 100 | 104.22 ± 3.15 | N.S |
| | 200 | 104.11 ± 2.66 | N.S |
| C. Example 3 | 100 | 99.67 ± 3.17 | N.S |
| | 200 | 95.44 ± 4.03 | N.S |
| Positive Control (0.1% SDS) | | 15.11 ± 1.72 | <0.01 |

TABLE 6

| Derivative | Treatment conc. (μM) | Viability of LNCaP relative to negative control 1% methyl-β-cyclodextrin (%) | Statistical significance |
|---|---|---|---|
| Example 9 | 100 | 91.33 ± 10.73 | N.S |
| | 200 | 45.33 ± 5.61 | <0.02 |
| Example 10 | 100 | 28.33 ± 3.18 | <0.02 |
| | 200 | 22.33 ± 2.33 | <0.02 |
| Example 11 | 100 | 37.00 ± 0.58 | <0.02 |
| | 200 | 30.67 ± 0.67 | <0.02 |
| Example 12 | 100 | 29.67 ± 1.20 | <0.02 |
| | 200 | 30.33 ± 0.88 | <0.02 |
| Example 13 | 100 | 72.33 ± 5.84 | <0.02 |
| | 200 | 66.33 ± 5.24 | <0.02 |
| Example 14 | 100 | 33.00 ± 1.53 | <0.02 |
| | 200 | 30.33 ± 0.67 | <0.02 |
| Example 15 | 100 | 64.25 ± 3.52 | <0.02 |
| | 200 | 36.50 ± 1.94 | <0.02 |
| Example 16 | 100 | 18.25 ± 0.63 | <0.02 |
| | 200 | 18.50 ± 0.50 | <0.02 |
| C. Example 1 | 100 | 105.64 ± 4.03 | N.S |
| | 200 | 93.64 ± 4.20 | N.S |
| C. Example 2 | 100 | 99.22 ± 6.11 | N.S |
| | 200 | 84.78 ± 6.16 | N.S |
| C. Example 3 | 100 | 92.89 ± 4.33 | N.S |
| | 200 | 90.22 ± 4.03 | N.S |
| Positive Control (0.1% SDS) | | 20.45 ± 1.58 | <0.01 |

Figure 3:
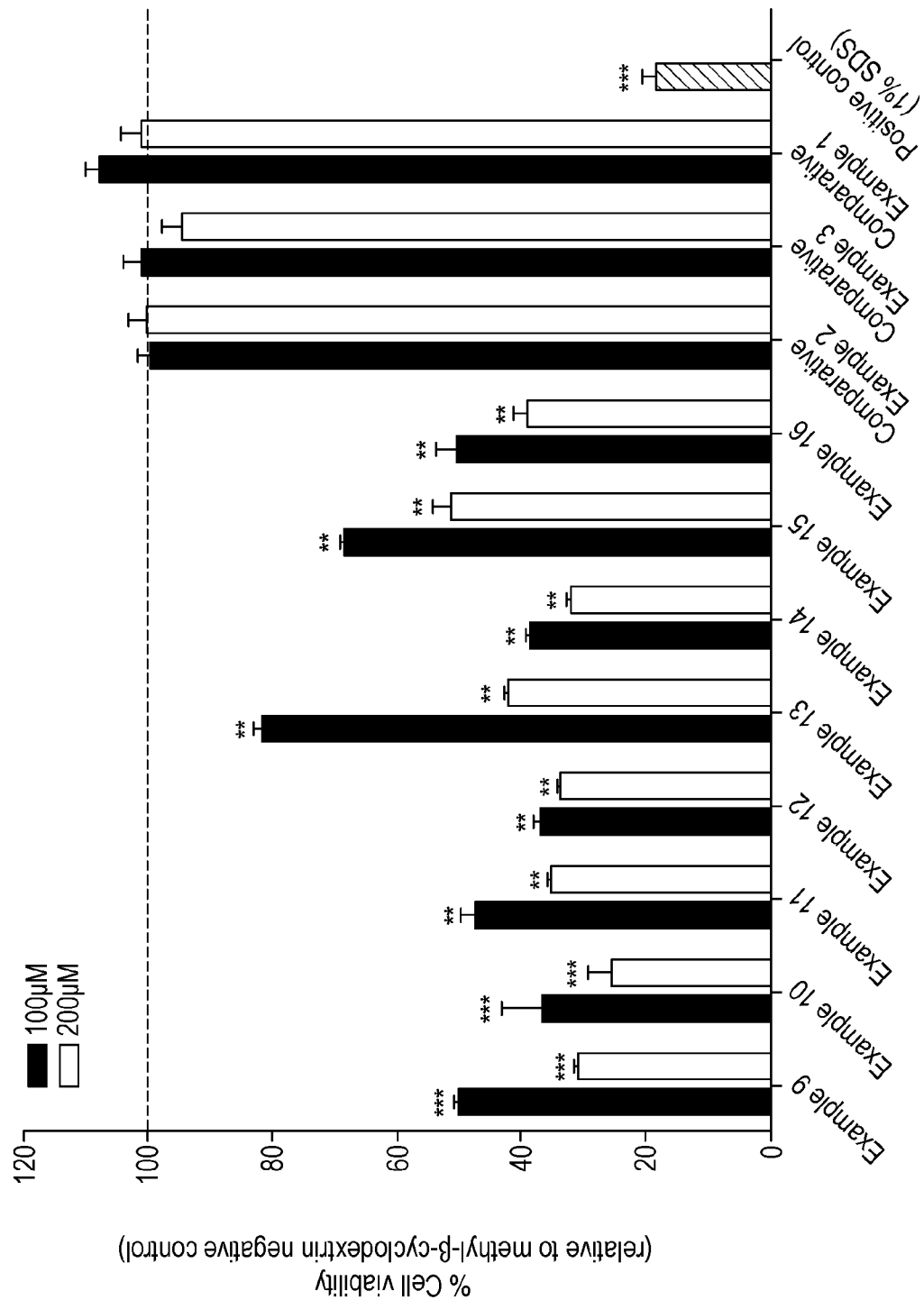
FIG. 3 is a graph showing the cell viability (%) of the prostate cancer cell line DU-145 after treatment with compositions of the Examples and the Comparative Examples, compared to the negative control 1% methyl-β-cyclodextrin.
Figure 4:
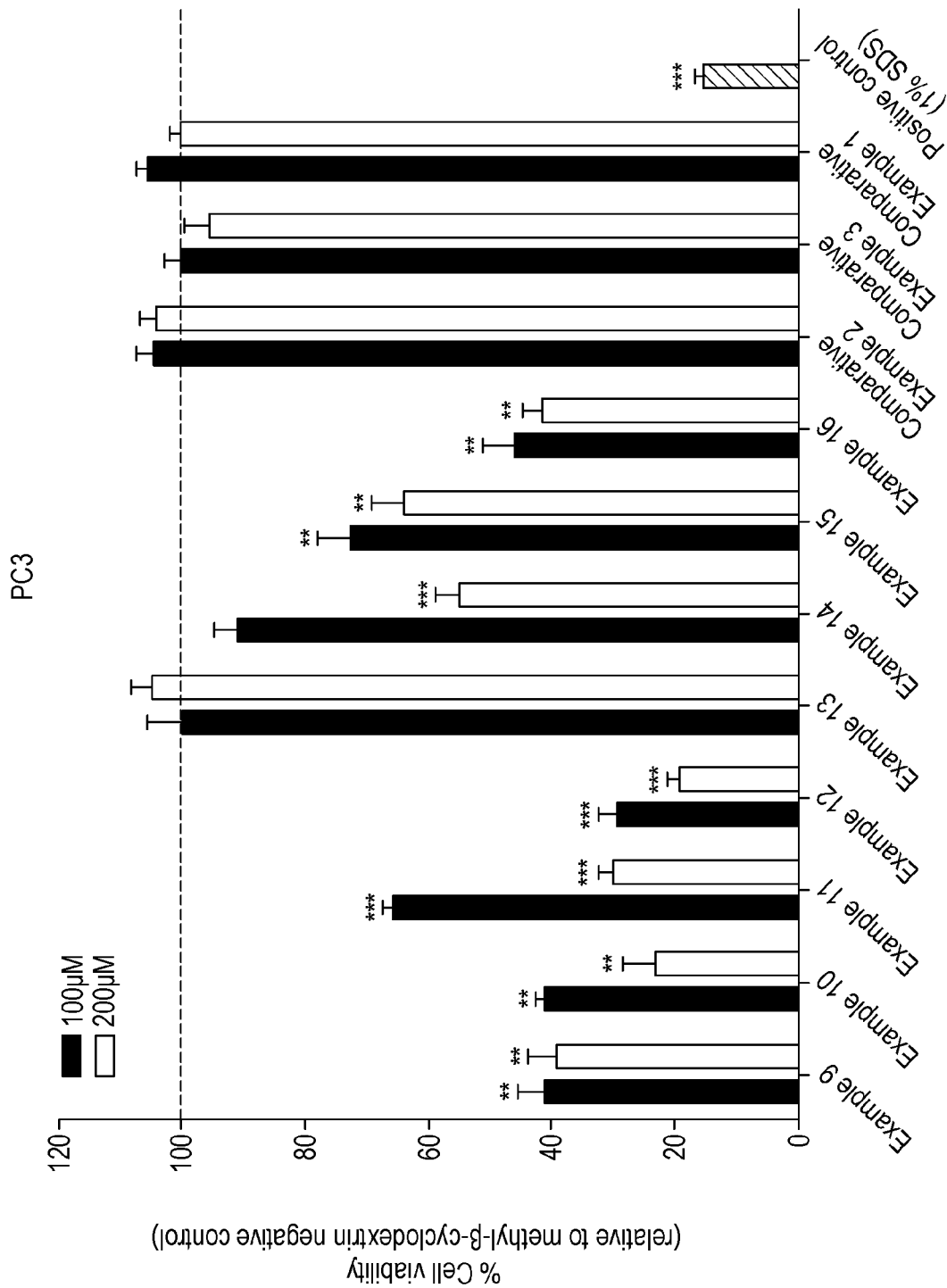
FIG. 4 is a graph showing the cell viability (%) of the prostate cancer cell line PC3 after treatment with compositions of the Examples and the Comparative Examples, compared to the negative control 1% methyl-β-cyclodextrin.
Figure 5:
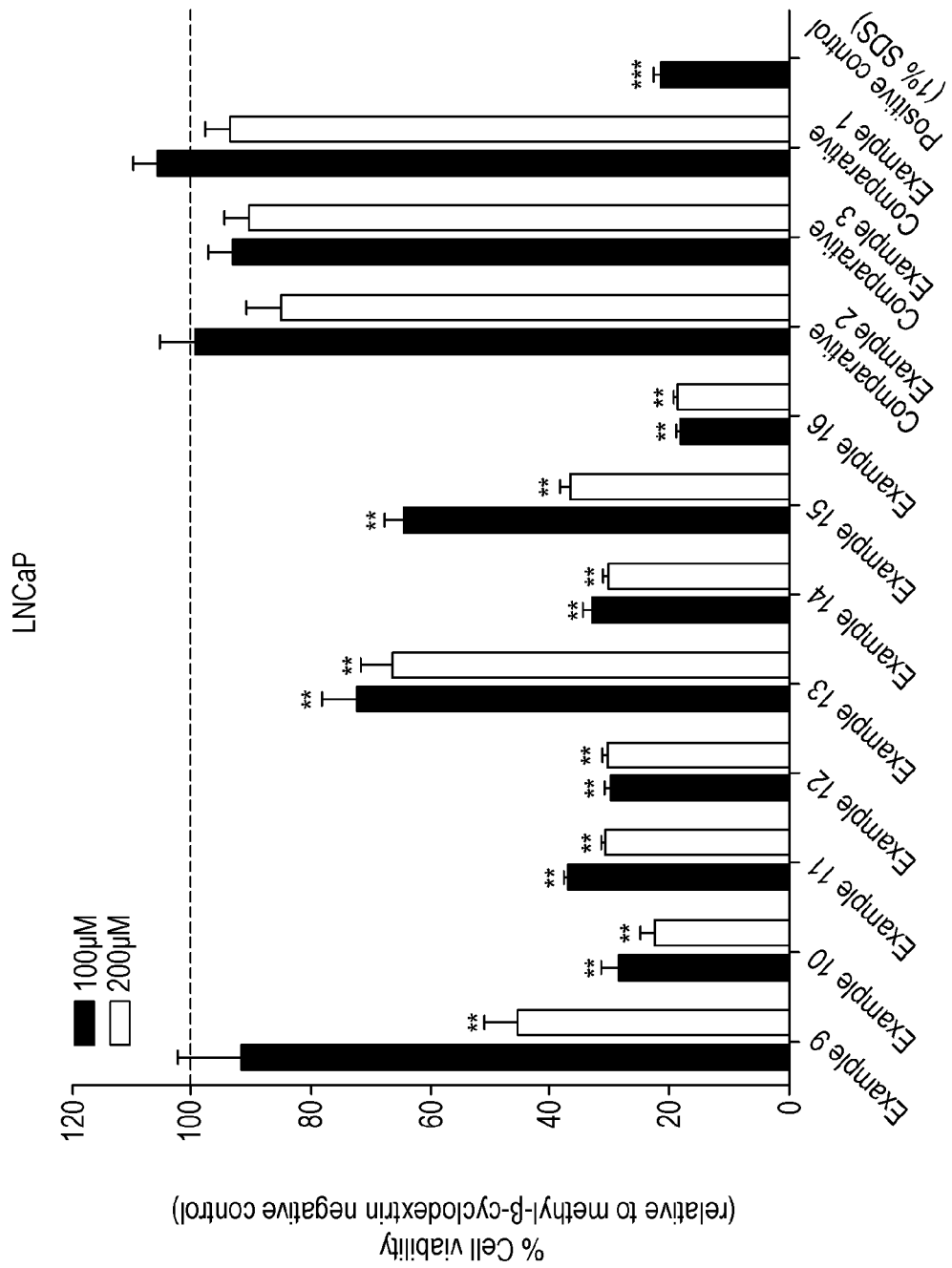
FIG. 5 is a graph showing the cell viability (%) of the prostate cancer cell line LNCaP after treatment with compositions of the Examples and the Comparative Examples, compared to the negative control 1% methyl-β-cyclodextrin.

With reference to Tables 4 to 6 and FIGS. 3 to 5, the pharmaceutical compositions (Examples 9 to 16) comprising the fatty acid-conjugated GnRH derivative according to an embodiment of the present disclosure (Examples 1 to 8) exhibited unpredictably excellent effects, compared to natural GnRH (Comparative Example 1) and the commercially available GnRH derivatives (Comparative Examples 2 and 3).

In detail, the prostate cell line DU-145 survived the compositions of Comparative Examples 1 to 3 at substantially the same rates as the negative control. Only the composition of Comparative Example 3 allowed a viability of about 94% for the cells. In contrast, the compositions according to an embodiment of the present disclosures reduced the cell viability to at least about 80% and to down to about 25%, compared to the negative control. The remarkably reduced cell viabilities by the compositions according to an embodiment of the present disclosure were statistically significant.

For PC3 prostate cancer cells, the compositions of Comparative Examples 1 to 3 showed slight reducing effects on cell viability. Only the triptorelin of Comparative Example 3 allowed about 95% for the cell viability. In contrast, the compositions according to an embodiment of the present disclosure showed a very significant reduction in the cell viability. Inter alia, the composition of Example 12 exhibited very highly reduced cell viability, compared to those of the Comparative Examples. Particularly, the composition of Example 12 reduced the cell viability to a similar degree to that which the positive control achieved.

When applied at a concentration of 200 μM to LNCaP cells, the compositions of Comparative Examples 1, 2, and 3 allowed cell viabilities of about 93%, about 85%, and about 90%, respectively. However, the compositions according to an embodiment of the present disclosure showed very high cell death effects, compared to the compositions of the Comparative Examples. Particularly, the cell death effect was found to be similar between the composition of Example 10 and the positive control and higher in the composition of Example 16 than the positive control.

According to the experimental data on the three different prostate cancer cell lines, the compositions of Examples 10, 12, 14, and 16 comprising the derivatives of Examples 2, 4, 6, and 8 in which the amino acid at position 1 is substituted from glutamic acid to glutamine were superior in cell death effect to those of Examples 9, 11, 13, and 15 comprising the derivatives of Examples 1, 3, 5, and 7 in which the amino acid at position 1 remains intact. These data indicate that the GnRH derivatives characterized by amino acid substitution at position 1, fatty acid conjugation, and conversion to salt according to an embodiment of the present disclosure exhibit an unpredictably excellent prostate cancer cell death effect.

Experimental Example 3 Assay for Ovarian Morphological Change

Experiments were carried out to examine whether or not the fatty acid-conjugated GnRH derivatives maintain the functional characteristics and incur a morphological change in the ovary.

The pharmaceutical compositions of Examples 9, 10, 13, 14, 15, and 16 were each subcutaneously injected at a single dose of 12.5 mg/kg once at the back of the neck to female rats 9 weeks old. Rats to which no drugs were administered were used as a non-treated control while an aqueous solution of 3 mg of methyl-β-cyclodextrin was injected to a negative control. Each group consisted of 3 rats.

On day 28 after injection, the rats were subjected to an autopsy to excise the ovaries which were then stained with hematoxylin-eosin (H&E stain). The stained ovaries were observed for histological change and pathogenic aberration.

Briefly, ovaries were stained with H&E and observed as follows.

1. Immediately after autopsy, the excised tissue (ovary) was fixed for 12 hours in a fixation solution.
2. The sufficiently fixed tissue was washed with water to remove the fixation reagent.
3. For use in paraffin embedding, the ovarian tissue was dehydrated with graded alcohols. The dehydration was conducted in a series of gradually graded alcohols beginning from a low concentration to higher concentrations and finally with 100% pure alcohol and benzene.

4. A solution of paraffin in benzene was allowed to infiltrate into the dehydrated ovarian tissue which was then treated with pure paraffin in a liquid state at a high temperature (60° C.) to completely infiltrate paraffin into the tissue.

5. The paraffin-embedded tissue was cut into blocks of suitable sizes and then sectioned at a 4 μm thickness on a microtome.

6. The sectioned tissue was mounted on a glass slide and deparaffinized with an organic solvent such as xylene.

7. The slide having the tissue attached thereto was hydrated by treatment with a series of alcohols from high to low concentrations.

8. An aqueous hematoxylin solution was first applied to stain the nucleus and other acidic structures (RNA-rich structures, etc.) blue.

9. Various substances and organelles in the cytoplasm and extracellular matrix were secondarily stained red with eosin.

10. After completion of the staining, the specimen was dehydrated with graded alcohols and then cover-slipped using an adhesive such as a resin (balsam or a synthetic resin). This process is called mounting.

11. After finishing the above procedures, the specimen slides were scanned using a ScanScope® AT slider scanner (Aperio) and the images thus stored were analyzed using the ImageScope program (Aperio). The scanned images are depicted in FIGS. 6 to 9.

Results

In female rats, an estrous cycle of diestrus, proestrus, estrus, and metestrus lasts about 4 to 5 days, with the ovary morphologically changing depending on the estrous stages.

It is known that when administered to rats, a GnRH agonist reduces the formation of secondary follicles and Graafian follicles (see: Mohammadbeigi et al., Short-term Administration of Gonadotropin-releasing Hormone Agonist (Buserelin) Induces Apoptosis in Rat Ovarian Developmental Follicles, July 2016). In this experiment, secondary and Graafian follicles on ovary images in each treatment group were indicted by arrows to examine whether the number of the follicles is reduced or not.

Figure 6:
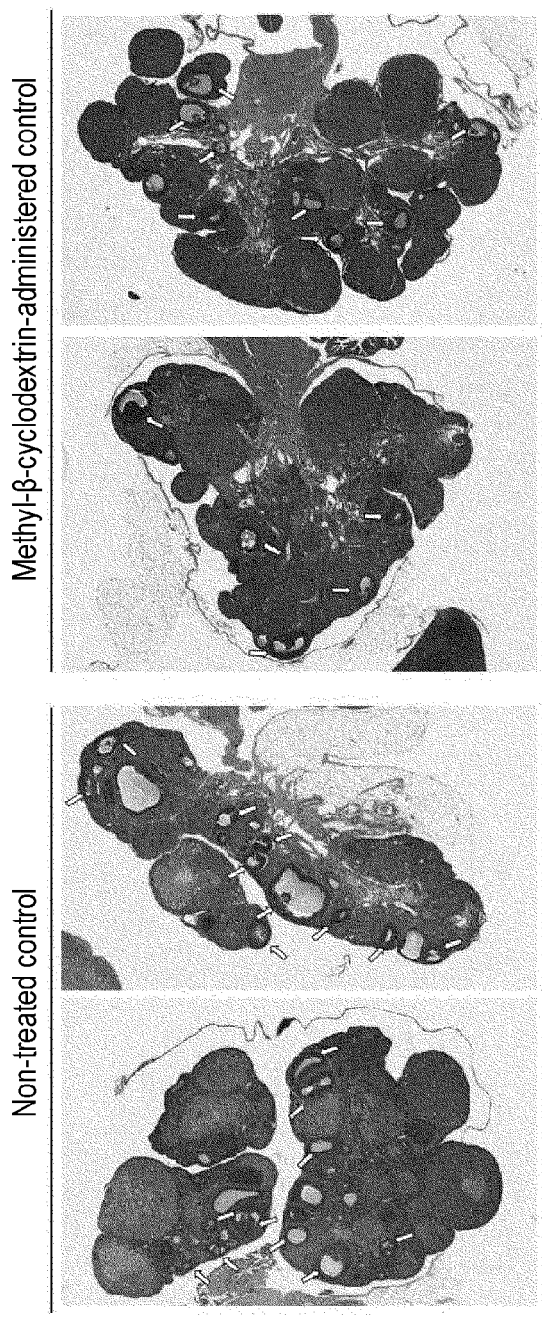
FIG. 6 shows ovary scan images of non-treated control and β-cyclodextrin-administered control after staining.
Figure 7:
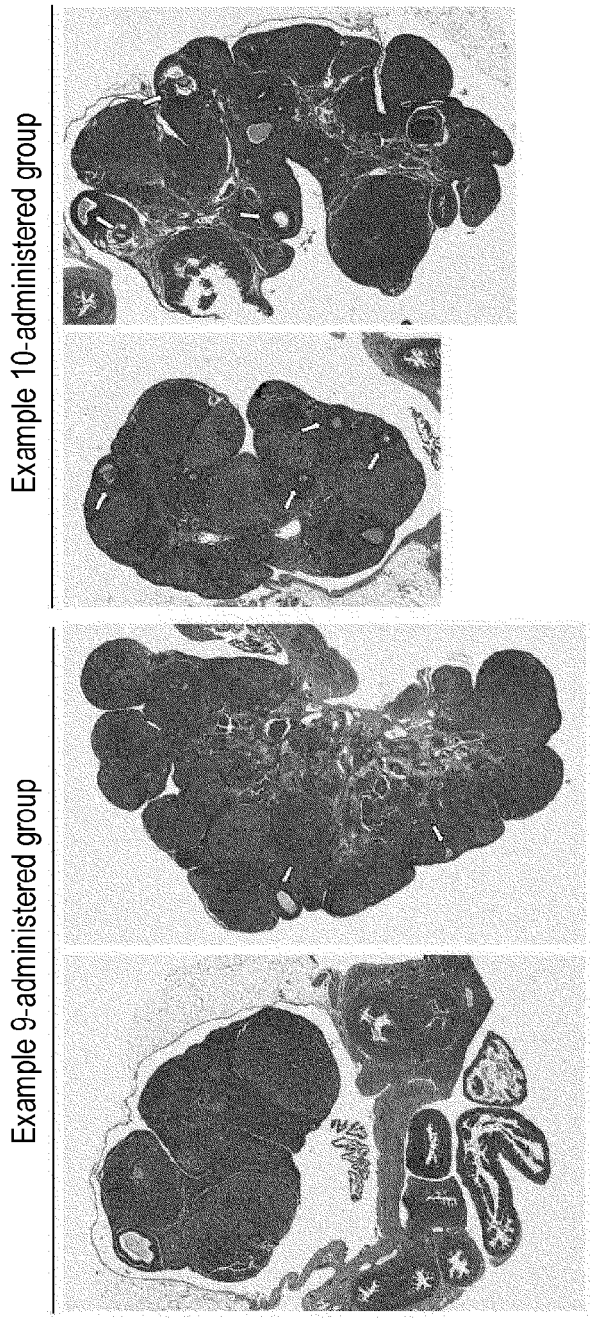
FIG. 7 shows ovary scan images of groups which were stained after administration of pharmaceutical compositions (Examples 9 and 10) comprising fatty acid-conjugated GnRH derivatives according to an embodiment of the present disclosure (Examples 1 and 2) thereto.
Figure 8:
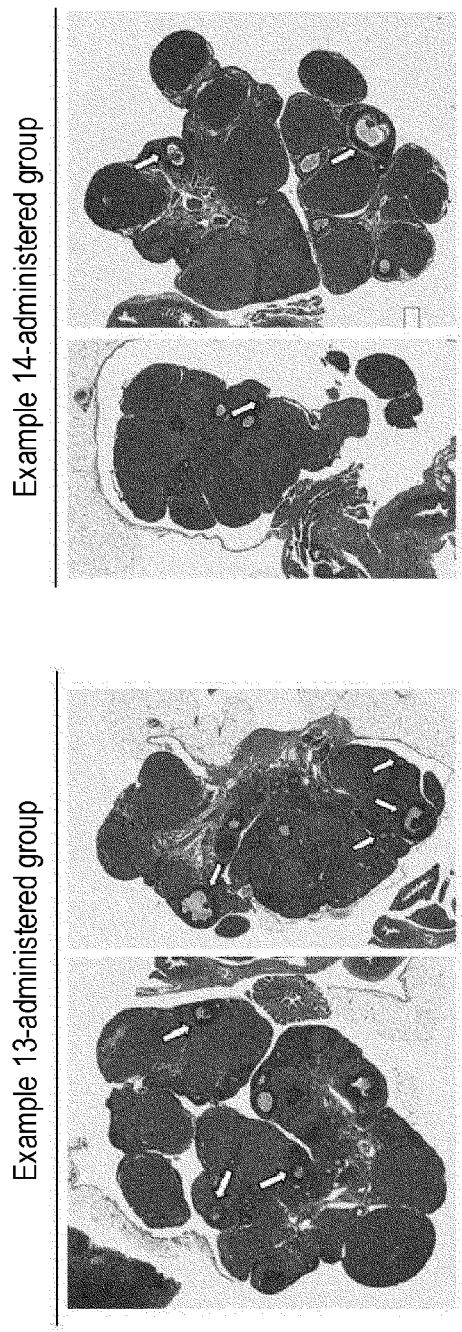
FIG. 8 shows ovary scan images of groups which were stained after administration of pharmaceutical compositions (Examples 13 and 14) comprising fatty acid-conjugated GnRH derivatives according to an embodiment of the present disclosure (Examples 5 and 6) thereto.
Figure 9:
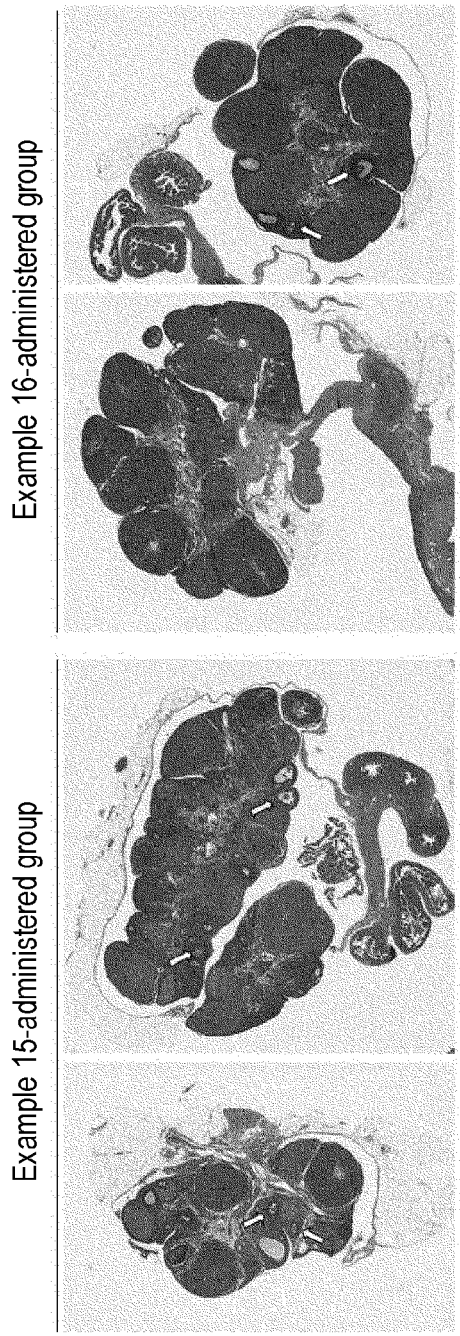
FIG. 9 shows ovary scan images of groups which were stained after administration of pharmaceutical compositions (Examples 15 and 16) comprising fatty acid-conjugated GnRH derivatives according to an embodiment of the present disclosure (Examples 7 and 8) thereto.

Referring to FIG. 6, many secondary or Graafian follicles were present in the non-treated group and the methyl-β-cyclodextrin-injected group as indicated by the arrows. In contrast, as shown in FIGS. 7 to 9, the numbers of secondary or Graafian follicles were decreased in the rat groups to which the fatty acid-conjugated GnRH derivatives according to an embodiment of the present disclosure (Examples 1, 2, 5, 6, 7, and 8) were administered. In the group to which the derivatives of the Examples were administered, corpus luteum was abundantly found and not many primordial follicles or multilaminar primary follicles were formed.

From the data, it is understood that the fatty acid-conjugated GnRH derivatives according to an embodiment of the present disclosure have an advantageous effect, specifically, an effect of deterring sexual maturation in rats.

In addition, the observation of a reduction in the number of secondary or Graafian follicles even 28 days after the single dose indicates that the fatty acid-conjugated GnRH derivatives according to an embodiment of the present disclosure or the inclusion complexes of the derivatives and cyclodextrin show sustained release and as such, can be used as long-acting formulations.

Experimental Example 4 Measurement of Rate of Increase of In Vivo Half-Life

The present inventor carried out animal experiments (female SD rats, nine weeks old) in order to examine the increased in vivo half-lives of the prepared fatty acid-conjugated GnRH derivatives. In brief, Leuprolide formulation for one-day administration (n=6), Leuprolide acetate depot formulation for one-month administration (3.75 mg/month; n=7), and the derivative of Example 4 (n=6) or the derivative of Example 6 (n=6) were subcutaneously administered once at a dose of 12.5 mg/kg to rats of each group, followed by monitoring blood concentrations over time. DMSO (dimethyl sulfoxide) was used as a solvent as needed. Before administration and at 0.5, 1, 2, and 6 hours and on days 1, 3, 7, 10, 14, 21, and 28 after administration, blood samples were taken from the tail vein of the rats and measured for the blood concentrations of Leuprolide and the derivatives of the Examples, using LC/MSMS. If the concentration reached about 4 ng/mL at a specific time point, no measurements were further made for the next time point.

The experimental results are summarized as follows. In the following table, the numerical unit is ng/mL.

TABLE 7

| Time | C. Example 1 (Leuprolide acetate 1-day formulation) | | C. Example 4 (Leuprolide acetate 1-month formulation (3.75 mg)) | | Example 4 (P2; Pal_[Q1] GnRH) | | Example 6 (P4; Pal_[Q1] GnRH_AcOH) | |
|---|---|---|---|---|---|---|---|---|
| | Mean | SD | Mean | SD | Mean | SD | Mean | SD |
| 0 | — | — | — | — | — | — | — | — |
| 0.5 hr | 1020 | 177 | 133 | 54.1 | 11.8 | 4.362 | 6.51 | 2.30 |
| 1 hr | 769 | 572 | 164 | 89.1 | 16.9 | 3.16 | 9.22 | 2.57 |
| 2 hr | 228 | 267 | 93.0 | 51.5 | 29.1 | 4.97 | 18.6 | 2.83 |
| 6 hr | 2.88 | 4.09 | 19.6 | 7.04 | 52.2 | 14.1 | 45.7 | 12.0 |
| 1 Day | — | — | 19.0 | 7.49 | 45.0 | 6.07 | 23.2 | 6.75 |
| 3 Days | — | — | 7.47 | 3.45 | 21.4 | 2.73 | 9.60 | 1.58 |
| 7 Days | — | — | 5.24 | 1.72 | 11.9 | 2.86 | 7.20 | 1.79 |
| 10 Days | — | — | 10.8 | 2.89 | 8.18 | 2.83 | 8.20 | 3.80 |
| 14 Days | — | — | 15.1 | 5.01 | 4.35 | 1.67 | 4.58 | 1.88 |
| 21 Days | — | — | 4.73 | 4.15 | — | — | 1.26 | 0.72 |
| 28 Days | — | — | 1.47 | 1.77 | — | — | — | — |

Figure 10:
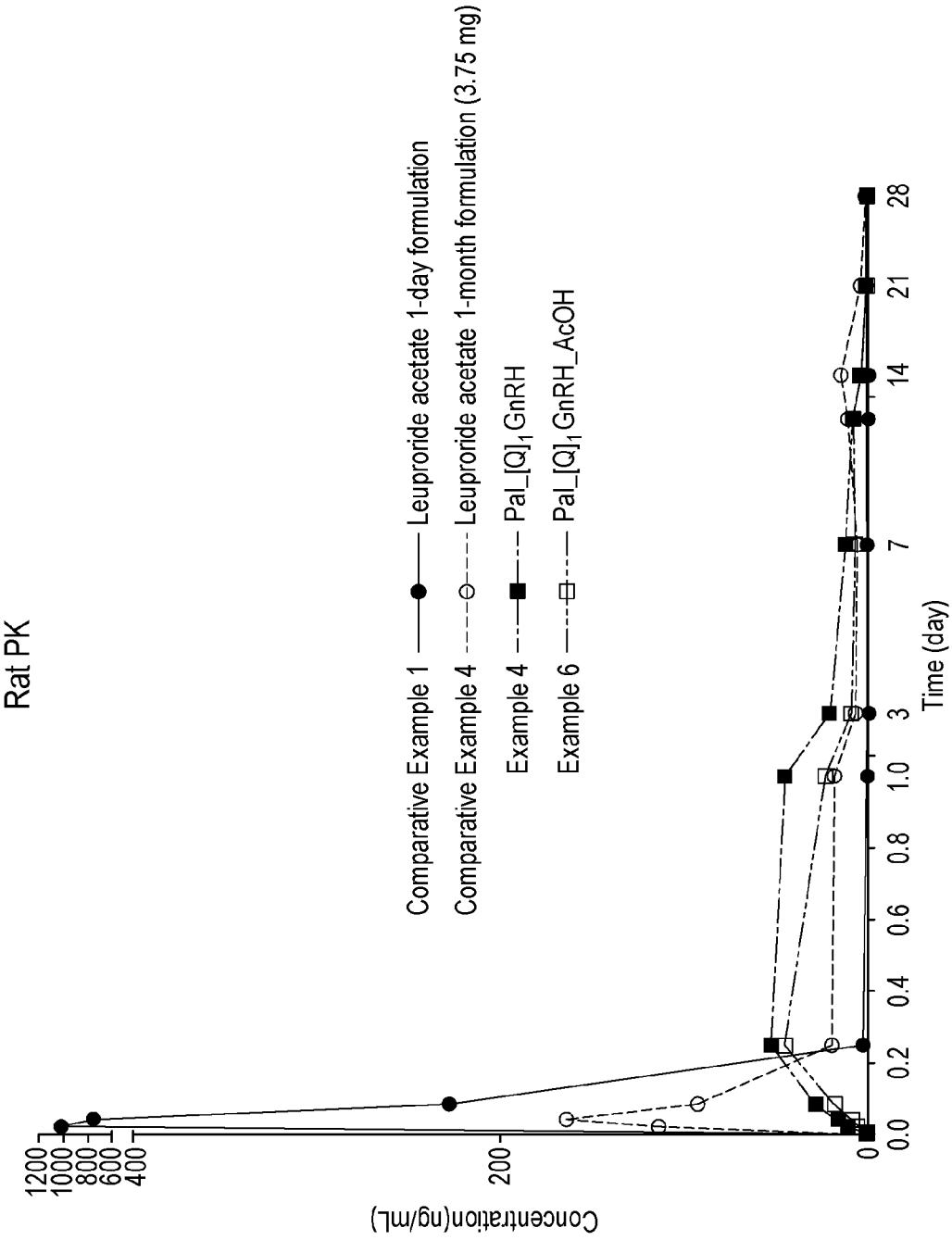
FIG. 10 is a graph showing the increased in vivo half-life of fatty acid-conjugated GnRH derivatives according to an embodiment of the present disclosure, where the blood concentration is plotted over time after the control drugs (Comparative Examples 1 and 4) and the fatty acid-conjugated GnRH derivatives according to an embodiment of the present disclosure are each subcutaneously administered once at a dose of 12.5 mg/kg to animals (rats).
Figure 11:
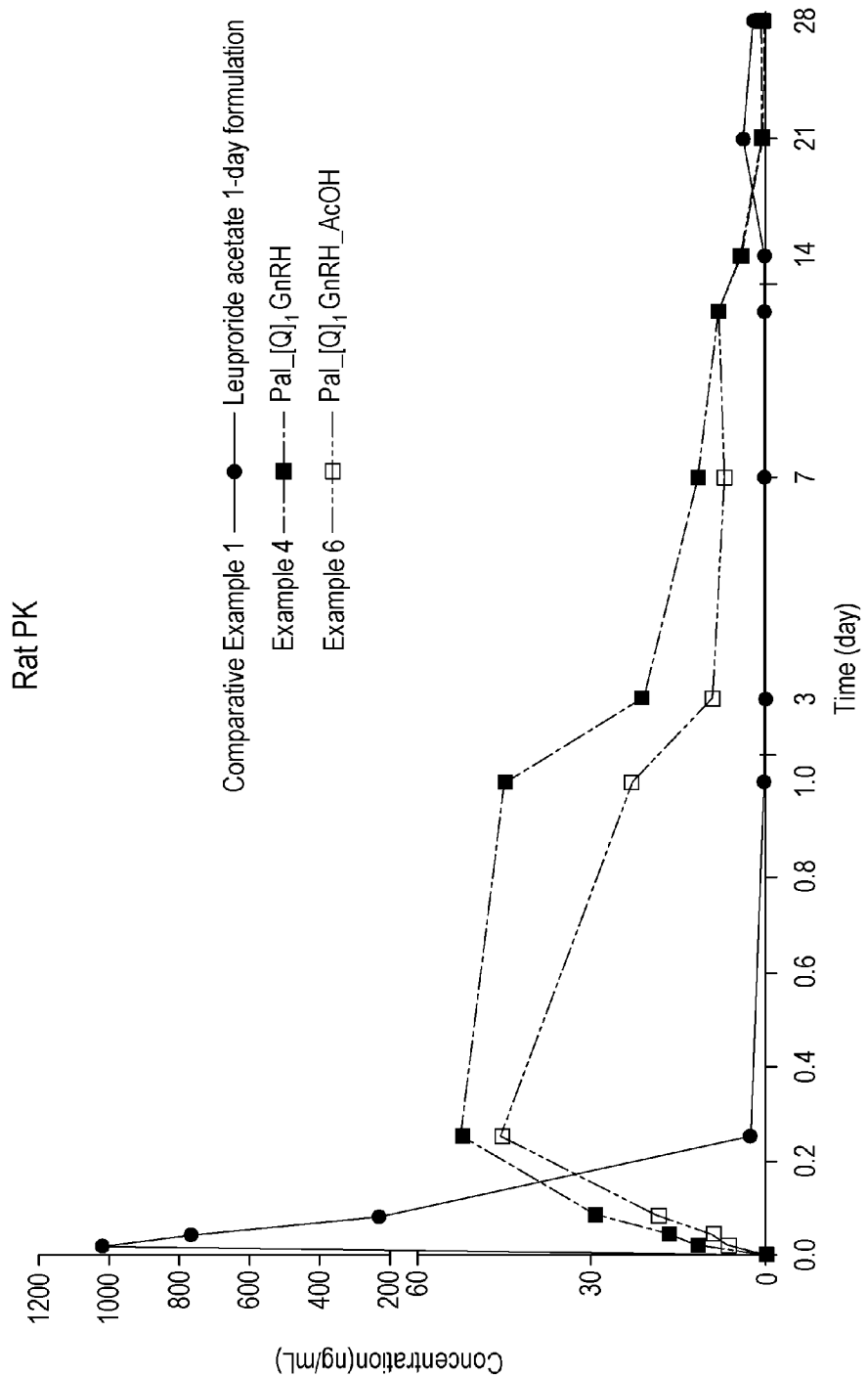
FIG. 11 is a graph showing the increased in vivo half-life of fatty acid-conjugated GnRH derivatives according to an embodiment of the present disclosure, where the blood concentration is plotted over time after the control drug Leuprolide acetate formulation for one-day administration (Comparative Example 1) and the fatty acid-conjugated GnRH derivatives according to an embodiment of the present disclosure (Examples 4 and 6) are each subcutaneously administered once at a dose of 12.5 mg/kg to animals (rats).
Figure 12:
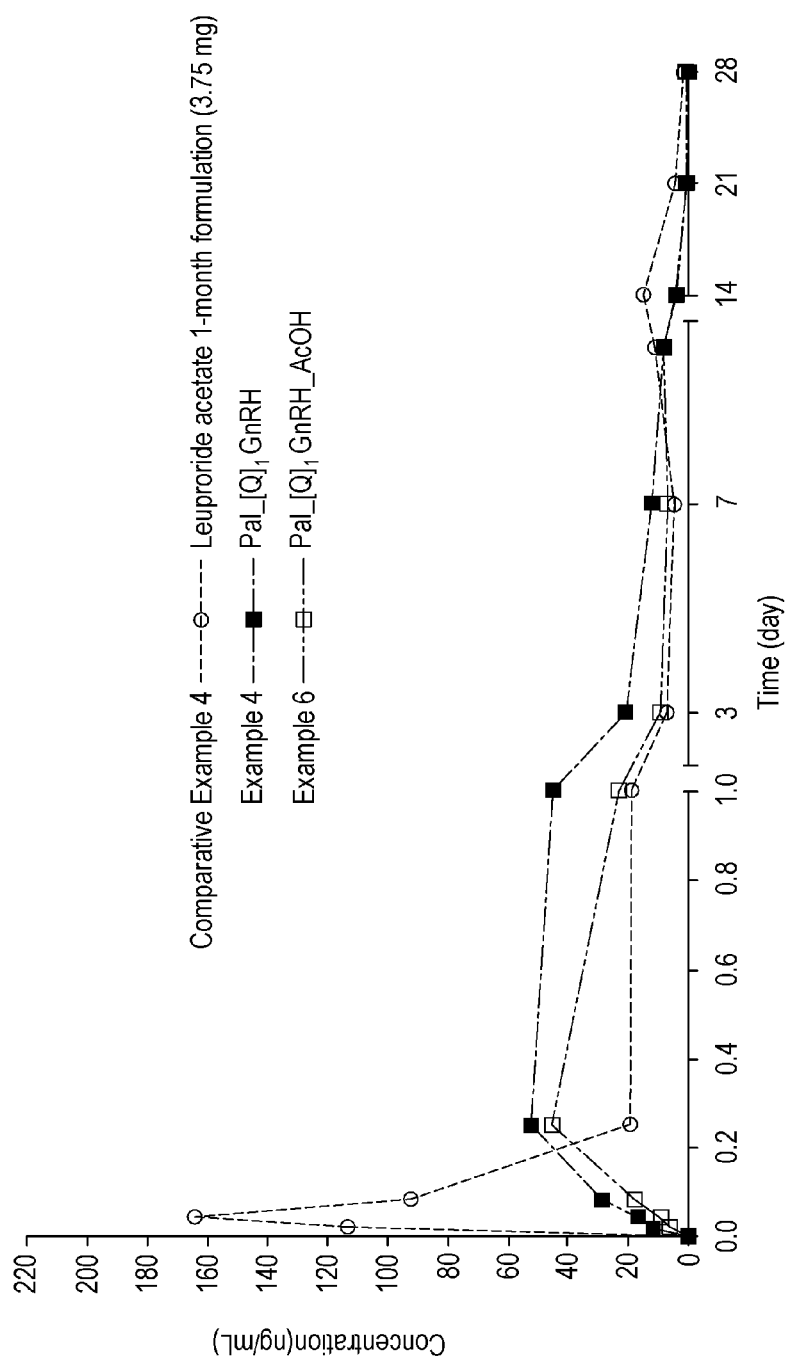
FIG. 12 is a graph showing the increased in vivo half-life of fatty acid-conjugated GnRH derivatives according to an embodiment of the present disclosure, where the blood concentration is plotted over time after the control drug Leuprolide Depot formulation for one-day administration (Comparative Example 4) and the fatty acid-conjugated GnRH derivatives according to an embodiment of the present disclosure (Examples 4 and 6) are each subcutaneously administered once at a dose of 12.5 mg/kg to animals (rats).

The measurement results are graphically depicted in FIGS. 10 to 12. Based on the results, pharmacokinetic analysis was carried out by calculating the half-life ($t_{1/2}$), clearance rate (CL), volume of distribution (Vd), time to reach the maximum concentration following drug administration (Tmax), maximum concentration following drug administration (Cmax), and systemic exposure to drug (AUCt). The analysis results are as follows.

TABLE 8

|  | C. Example 1 | C. Example 4 | Example 4 | Example 6 |
|---|---|---|---|---|
| $t_{1/2}$ [Day] | 0.03 | 4.17 | 4.80 | 4.03 |
| CL [(mg/kg)/(ng/mL)/Day] | 0.180 | 0.049 | 0.051 | 0.075 |
| Vd [(mg/kg)/(ng/mL)] | 0.007 | 0.296 | 0.351 | 0.436 |
| Tmax [Day] | 0.02 | 0.04 | 0.25 | 0.25 |
| Cmax [ng/mL] | 1020.0 | 164.0 | 52.2 | 45.7 |
| AUCt [ng/mL*d] | 69.21 | 245.22 | 216.24 | 159.51 |

As can be understood from the data, the fatty acid-conjugated GnRH derivatives according to an embodiment of the present disclosure are significantly superior to Leuprolide (Comparative Example 1) in terms of the in vivo half-life, clearance rate, volume of distribution, and systemic exposure (AUCt). Furthermore, the fatty acid-conjugated GnRH derivatives according to an embodiment of the present disclosure were found to have similar levels of half-life, clearance rate, and systemic exposure (AUCt) to those of the existing Leuprolide formulation for one-month administration containing a physically mixed biodegradable polymer and particularly to exhibit a superior volume of distribution, a delayed time to reach the maximum concentration following drug administration, and a reduced maximum concentration for a prolonged period of time, compared to the commercially available product. Taken together, the data demonstrate that the fatty acid-conjugated GnRH derivatives according to an embodiment of the present disclosure allow GnRH to maintain a suitable concentration for a prolonged period of time in vivo.

In light of the excellent properties thereof, the fatty acid-conjugated GnRH derivatives according to an embodiment of the present disclosure can be used at a remarkably reduced volume, compared to the existing products in which biodegradable polymers are mixed with GnRH derivatives to achieve a sustained release, and thus can overcome the disadvantage of pain and exclude the side effect that the biodegradable polymer remains in vivo for a long period of time. These properties are advantageous particularly to children. In addition, having excellent release sustainability, the fatty acid-conjugated GnRH derivatives according to an embodiment of the present disclosure can exhibit excellent effects of killing prostate cancer cells as well as deterring sexual maturation by reducing the numbers of secondary or graafian follicles in the ovary, as identified in Experimental Examples 2 and 3.

Meanwhile, when the fatty acid-conjugated GnRH derivatives according to an embodiment of the present disclosure were used in combination with the biodegradable polymer used in the conventional products, the half-life is remarkably increased, compared to conventional drugs such as Leuprolide, to become as long as drugs used in invasive methods (surgery), such as for implants (several months to one year).

Although the technical idea of the present disclosure has been described by the examples described in some embodiments and illustrated in the accompanying drawings, it should be noted that various substitutions, modifications, and changes can be made without departing from the scope of the present disclosure which can be understood by those skilled in the art to which the present disclosure pertains. In addition, it should be noted that such substitutions, modifications and changes are intended to fall within the scope of the appended claims.

What is claimed is:

1. A pharmaceutical composition for preventing or treating a sex hormone-dependent disease, the pharmaceutical composition comprising:
a long-acting fatty acid-conjugated gonadotropin-releasing hormone (GnRH) derivative in which the gonadotropin-releasing hormone (GnRH) derivative is conjugated with a fatty acid, or a pharmaceutically acceptable salt thereof as an active ingredient; and
cyclodextrin,
wherein the GnRH derivative comprises an amino acid sequence selected form the group consisting of SEQ ID NO: 2, and SEQ ID NOS: 4 to 11,
wherein the fatty acid is a lauric acid, palmitic acid or arachidic acid,
wherein a carboxyl group of the fatty acid of the GnRH derivative is conjugated through a peptide-bond to an amino terminus of the peptide portion of the GnRH derivative.

2. The pharmaceutical composition of claim 1, wherein the pharmaceutically acceptable salt is selected from the group consisting of inorganic acids, organic acids, ammonium salts, alkali metal salts, and alkaline earth metal salts.

3. The pharmaceutical composition of claim 2, wherein the pharmaceutically acceptable salt is selected from the group consisting of hydrochloride, hydrobromide, phosphate, metaphosphate, nitrate, sulfate, acetate, sulfonate, benzoate, citrate, ethanesulfonate, fumarate, lactate, maleate, malate, succinate, tartrate, sodium salt, calcium salt, potassium salt, and magnesium salt.

4. The pharmaceutical composition of claim 1, wherein the sex hormone-dependent disease is selected from the group consisting of prostate cancer, breast cancer, ovarian cancer, endometriosis, uterine fibroid, polycystic ovary disease, central precocious puberty, hypertrichosis, gonadotroph pituitary adenoma, sleep apnea, irritable bowel syndrome, premenstrual syndrome, benign prostatic hyperplasia, and contraception.

5. The pharmaceutical composition of claim 1, wherein the cyclodextrin is methyl-β-cyclodextrin.

6. The pharmaceutical composition of claim 1, wherein the fatty acid-conjugated GnRH derivative and the cyclodextrin exist together as an inclusion complex.

7. The pharmaceutical composition of claim 1, wherein the cyclodextrin and the fatty acid-conjugated GnRH derivative are used at a molar ratio of 7:1 to 1:1.

8. The pharmaceutical composition of claim 1, wherein the pharmaceutical composition further comprises a biodegradable polymer.

9. A method for preventing or treating a sex hormone-dependent disease, comprising administering a pharmaceutical composition to a patient in need thereof,
wherein the pharmaceutical composition comprising:
a long-acting fatty acid-conjugated gonadotropin-releasing hormone (GnRH) derivative in which the gonadotropin-releasing hormone (GnRH) derivative is conjugated with a fatty acid, or a pharmaceutically acceptable salt thereof as an active ingredient; and
cyclodextrin,
wherein the GnRH derivative comprises an amino acid sequence selected form the group consisting of SEQ ID NO: 2, and SEQ ID NOS: 4 to 11,
wherein the fatty acid is a lauric acid, palmitic acid or arachidic acid,
wherein a carboxyl group of the fatty acid of the GnRH derivative is conjugated through a peptide-bond to an amino terminus of the peptide portion of the GnRH derivative.

10. The method of claim 9, wherein the pharmaceutically acceptable salt is selected from the group consisting of inorganic acids, organic acids, ammonium salts, alkali metal salts, and alkaline earth metal salts.

11. The method of claim 10, wherein the pharmaceutically acceptable salt is selected from the group consisting of hydrochloride, hydrobromide, phosphate, metaphosphate, nitrate, sulfate, acetate, sulfonate, benzoate, citrate, ethanesulfonate, furmarate, lactate, maleate, malate, succinate, tartrate, sodium salt, calcium salt, potassium salt, and magnesium salt.

12. The method of claim 9, wherein the sex hormone-dependent disease is selected from the group consisting of prostate cancer, breast cancer, ovarian cancer, endometriosis, uterine fibroid, polycystic ovary disease, central precocious puberty, hypertrichosis, gonadotroph pituitary adenoma, sleep apnea, irritable bowel syndrome, premenstrual syndrome, benign prostatic hyperplasia, and contraception.

13. The method of claim 9, wherein the cyclodextrin is methyl-β-cyclodextrin.

14. The method of claim 9, wherein the fatty acid-conjugated GnRH derivative and the cyclodextrin exist together as an inclusion complex.

15. The method of claim 9, wherein the cyclodextrin and the fatty acid-conjugated GnRH derivative are used at a molar ratio of 7:1 to 1:1.

16. The method of claim 9, wherein the pharmaceutical composition further comprises a biodegradable polymer.

\* \* \* \* \*

SEQUENCE LISTING

```
<160> NUMBER OF SEQ ID NOS: 11

<210> SEQ ID NO 1
<211> LENGTH: 10
<212> TYPE: PRT
<213> ORGANISM: homo sapiens
<220> FEATURE:
<221> NAME/KEY: SITE
<222> LOCATION: (1)..(1)
<223> OTHER INFORMATION: Glu in position 1 is pyroGlu.

<400> SEQUENCE: 1

Glu His Trp Ser Tyr Gly Leu Arg Pro Gly
1               5                   10

<210> SEQ ID NO 2
<211> LENGTH: 9
<212> TYPE: PRT
<213> ORGANISM: Artificial Sequence
<220> FEATURE:
<223> OTHER INFORMATION: GnRH analogue-Leuprolide
<220> FEATURE:
<221> NAME/KEY: SITE
<222> LOCATION: (1)..(1)
<223> OTHER INFORMATION: Glu in position 1 is pyroGlu.
<220> FEATURE:
<221> NAME/KEY: SITE
<222> LOCATION: (6)..(6)
<223> OTHER INFORMATION: Leu in position 6 is D-Leu.
<220> FEATURE:
<221> NAME/KEY: SITE
<222> LOCATION: (9)..(9)
<223> OTHER INFORMATION: C-terminal of the peptide was modified as
      NHEt(des-Gly).
```

```
<400> SEQUENCE: 2

Glu His Trp Ser Tyr Leu Leu Arg Pro
1               5

<210> SEQ ID NO 3
<211> LENGTH: 10
<212> TYPE: PRT
<213> ORGANISM: Artificial Sequence
<220> FEATURE:
<223> OTHER INFORMATION: GnRH analogue-Triptorelin
<220> FEATURE:
<221> NAME/KEY: SITE
<222> LOCATION: (1)..(1)
<223> OTHER INFORMATION: Glu in position 1 is pyroGlu.
<220> FEATURE:
<221> NAME/KEY: SITE
<222> LOCATION: (6)..(6)
<223> OTHER INFORMATION: Trp in position 6 is D-Trp

<400> SEQUENCE: 3

Glu His Trp Ser Tyr Trp Leu Arg Pro Gly
1               5                   10

<210> SEQ ID NO 4
<211> LENGTH: 9
<212> TYPE: PRT
<213> ORGANISM: Artificial Sequence
<220> FEATURE:
<223> OTHER INFORMATION: GnRH analogue
<220> FEATURE:
<221> NAME/KEY: SITE
<222> LOCATION: (1)..(1)
<223> OTHER INFORMATION: Glu in position 1 was modified with Lauric
      acid.
<220> FEATURE:
<221> NAME/KEY: PEPTIDE
<222> LOCATION: (1)..(9)
<223> OTHER INFORMATION: The petide was salificated with acetate salt.
<220> FEATURE:
<221> NAME/KEY: SITE
<222> LOCATION: (6)..(6)
<223> OTHER INFORMATION: Leu in position 6 is D-Leu.
<220> FEATURE:
<221> NAME/KEY: SITE
<222> LOCATION: (9)..(9)
<223> OTHER INFORMATION: C-terminus of the peptide was modified as
      NHEt(des-Gly).

<400> SEQUENCE: 4

Glu His Trp Ser Tyr Leu Leu Arg Pro
1               5

<210> SEQ ID NO 5
<211> LENGTH: 9
<212> TYPE: PRT
<213> ORGANISM: Artificial Sequence
<220> FEATURE:
<223> OTHER INFORMATION: GnRH analogue
<220> FEATURE:
<221> NAME/KEY: SITE
<222> LOCATION: (1)..(1)
<223> OTHER INFORMATION: Gln in position 1 was modified with Lauric
      acid.
<220> FEATURE:
<221> NAME/KEY: PEPTIDE
<222> LOCATION: (1)..(9)
<223> OTHER INFORMATION: The petide was salificated with acetate salt.
<220> FEATURE:
<221> NAME/KEY: SITE
<222> LOCATION: (6)..(6)
<223> OTHER INFORMATION: Leu in position 6 is D-Leu.
<220> FEATURE:
<221> NAME/KEY: SITE
```

<222> LOCATION: (9)..(9)
<223> OTHER INFORMATION: C-terminus of the peptide was modified as
      NHEt(des-Gly).

<400> SEQUENCE: 5

Gln His Trp Ser Tyr Leu Leu Arg Pro
1               5

<210> SEQ ID NO 6
<211> LENGTH: 9
<212> TYPE: PRT
<213> ORGANISM: Artificial Sequence
<220> FEATURE:
<223> OTHER INFORMATION: GnRH analogue
<220> FEATURE:
<221> NAME/KEY: SITE
<222> LOCATION: (1)..(1)
<223> OTHER INFORMATION: Glu in position 1 was modified with Palmitic
      acid.
<220> FEATURE:
<221> NAME/KEY: PEPTIDE
<222> LOCATION: (1)..(9)
<223> OTHER INFORMATION: The petide was salificated with sodium salt.
<220> FEATURE:
<221> NAME/KEY: SITE
<222> LOCATION: (6)..(6)
<223> OTHER INFORMATION: Leu in position 6 is D-Leu.
<220> FEATURE:
<221> NAME/KEY: SITE
<222> LOCATION: (9)..(9)
<223> OTHER INFORMATION: C-terminus of the peptide was modified as
      NHEt(des-Gly).

<400> SEQUENCE: 6

Glu His Trp Ser Tyr Leu Leu Arg Pro
1               5

<210> SEQ ID NO 7
<211> LENGTH: 9
<212> TYPE: PRT
<213> ORGANISM: Artificial Sequence
<220> FEATURE:
<223> OTHER INFORMATION: GnRH analogue
<220> FEATURE:
<221> NAME/KEY: SITE
<222> LOCATION: (1)..(1)
<223> OTHER INFORMATION: Gln in position 1 was modified with Palmitic
      acid.
<220> FEATURE:
<221> NAME/KEY: PEPTIDE
<222> LOCATION: (1)..(9)
<223> OTHER INFORMATION: The petide was salificated with sodium salt.
<220> FEATURE:
<221> NAME/KEY: SITE
<222> LOCATION: (6)..(6)
<223> OTHER INFORMATION: Leu in position 6 is D-Leu.
<220> FEATURE:
<221> NAME/KEY: SITE
<222> LOCATION: (9)..(9)
<223> OTHER INFORMATION: C-terminus of the peptide was modified as
      NHEt(des-Gly).

<400> SEQUENCE: 7

Gln His Trp Ser Tyr Leu Leu Arg Pro
1               5

<210> SEQ ID NO 8
<211> LENGTH: 9
<212> TYPE: PRT
<213> ORGANISM: Artificial Sequence
<220> FEATURE:
<223> OTHER INFORMATION: GnRH analogue
<220> FEATURE:

```
<221> NAME/KEY: SITE
<222> LOCATION: (1)..(1)
<223> OTHER INFORMATION: Glu in position 1 was modified with Palmitic
      acid.
<220> FEATURE:
<221> NAME/KEY: PEPTIDE
<222> LOCATION: (1)..(9)
<223> OTHER INFORMATION: The petide was salificated with acetate salt.
<220> FEATURE:
<221> NAME/KEY: SITE
<222> LOCATION: (6)..(6)
<223> OTHER INFORMATION: Leu in position 6 is D-Leu.
<220> FEATURE:
<221> NAME/KEY: SITE
<222> LOCATION: (9)..(9)
<223> OTHER INFORMATION: C-terminus of the peptide was modified as
      NHEt(des-Gly).

<400> SEQUENCE: 8

Glu His Trp Ser Tyr Leu Leu Arg Pro
1               5

<210> SEQ ID NO 9
<211> LENGTH: 9
<212> TYPE: PRT
<213> ORGANISM: Artificial Sequence
<220> FEATURE:
<223> OTHER INFORMATION: GnRH analogue
<220> FEATURE:
<221> NAME/KEY: SITE
<222> LOCATION: (1)..(1)
<223> OTHER INFORMATION: Gln in position 1 was modified with Palmitic
      acid.
<220> FEATURE:
<221> NAME/KEY: PEPTIDE
<222> LOCATION: (1)..(9)
<223> OTHER INFORMATION: The petide was salificated with acetate salt.
<220> FEATURE:
<221> NAME/KEY: SITE
<222> LOCATION: (6)..(6)
<223> OTHER INFORMATION: Leu in position 6 is D-Leu.
<220> FEATURE:
<221> NAME/KEY: SITE
<222> LOCATION: (9)..(9)
<223> OTHER INFORMATION: C-terminus of the peptide was modified as
      NHEt(des-Gly).

<400> SEQUENCE: 9

Gln His Trp Ser Tyr Leu Leu Arg Pro
1               5

<210> SEQ ID NO 10
<211> LENGTH: 9
<212> TYPE: PRT
<213> ORGANISM: Artificial Sequence
<220> FEATURE:
<223> OTHER INFORMATION: GnRH analogue
<220> FEATURE:
<221> NAME/KEY: SITE
<222> LOCATION: (1)..(1)
<223> OTHER INFORMATION: Glu in position 1 was modified with Arachidic
      acid.
<220> FEATURE:
<221> NAME/KEY: PEPTIDE
<222> LOCATION: (1)..(9)
<223> OTHER INFORMATION: The petide was salificated with acetate salt.
<220> FEATURE:
<221> NAME/KEY: SITE
<222> LOCATION: (6)..(6)
<223> OTHER INFORMATION: Leu in position 6 is D-Leu.
<220> FEATURE:
<221> NAME/KEY: SITE
<222> LOCATION: (9)..(9)
<223> OTHER INFORMATION: C-terminus of the peptide was modified as
      NHEt(des-Gly).
```

```
<400> SEQUENCE: 10

Glu His Trp Ser Tyr Leu Leu Arg Pro
1               5

<210> SEQ ID NO 11
<211> LENGTH: 9
<212> TYPE: PRT
<213> ORGANISM: Artificial Sequence
<220> FEATURE:
<223> OTHER INFORMATION: GnRH analogue
<220> FEATURE:
<221> NAME/KEY: SITE
<222> LOCATION: (1)..(1)
<223> OTHER INFORMATION: Gln in position 1 was modified with Arachidic
      acid.
<220> FEATURE:
<221> NAME/KEY: PEPTIDE
<222> LOCATION: (1)..(9)
<223> OTHER INFORMATION: The petide was salificated with acetate salt.
<220> FEATURE:
<221> NAME/KEY: SITE
<222> LOCATION: (6)..(6)
<223> OTHER INFORMATION: Leu in position 6 is D-Leu.
<220> FEATURE:
<221> NAME/KEY: SITE
<222> LOCATION: (9)..(9)
<223> OTHER INFORMATION: C-terminus of the peptide was modified as
      NHEt(des-Gly).

<400> SEQUENCE: 11

Gln His Trp Ser Tyr Leu Leu Arg Pro
1               5
```